US012157763B2

(12) United States Patent
Lin et al.

(10) Patent No.: US 12,157,763 B2
(45) Date of Patent: *Dec. 3, 2024

(54) ANTIBODY SPECIFIC TO SPIKE PROTEIN OF SARS-CoV-2 AND USES THEREOF

(71) Applicant: ACADEMIA SINICA, Taipei (TW)

(72) Inventors: Kuo-I Lin, Taipei (TW); Che Ma, New Taipei (TW); Chi-Huey Wong, Taipei (TW); Szu-Wen Wang, Taipei (TW); Yi-Hsuan Chang, Taichung (TW); Xiaorui Chen, Taipei (TW); Han-Yi Huang, Taoyuan (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 18/403,419

(22) Filed: Jan. 3, 2024

(65) Prior Publication Data

US 2024/0228591 A1    Jul. 11, 2024

Related U.S. Application Data

(63) Continuation of application No. 17/937,744, filed on Oct. 3, 2022, now Pat. No. 11,866,485.

(60) Provisional application No. 63/251,472, filed on Oct. 1, 2021.

(51) Int. Cl.
*C07K 16/10* (2006.01)
*A61K 39/42* (2006.01)
*A61K 39/00* (2006.01)

(52) U.S. Cl.
CPC .............. *C07K 16/10* (2013.01); *A61K 39/42* (2013.01); *A61K 2039/505* (2013.01); *C07K 2317/14* (2013.01); *C07K 2317/21* (2013.01); *C07K 2317/24* (2013.01); *C07K 2317/31* (2013.01); *C07K 2317/34* (2013.01); *C07K 2317/41* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,871,626 | B2 | 1/2011 | Hoffmann et al. |
| 10,301,377 | B2 | 5/2019 | Graham et al. |
| 10,906,944 | B2 | 2/2021 | He et al. |
| 10,953,089 | B1 | 3/2021 | Smith et al. |
| 10,954,289 | B1 | 3/2021 | Babb et al. |
| 11,480,391 | B2 | 10/2022 | Wong et al. |
| 11,866,485 | B2 * | 1/2024 | Lin ................ C07K 16/1003 |
| 11,918,641 | B2 | 3/2024 | Wong et al. |
| 2010/0041740 | A1 | 2/2010 | Wong et al. |
| 2010/0247571 | A1 | 9/2010 | Wong et al. |
| 2015/0132330 | A1 | 5/2015 | Garcia-Sastre et al. |
| 2016/0199481 | A1 | 7/2016 | Bloom |
| 2016/0376321 | A1 | 12/2016 | Hotez et al. |
| 2018/0043007 | A1 | 2/2018 | LeFebvre et al. |
| 2020/0046826 | A1 | 2/2020 | Wong et al. |
| 2021/0017563 | A1 | 1/2021 | Bhatnagar et al. |
| 2023/0074185 | A1 | 3/2023 | Wong et al. |
| 2023/0105209 | A1 | 4/2023 | Lin et al. |
| 2023/0279080 | A1 | 9/2023 | Lin |
| 2023/0302114 | A1 | 9/2023 | Wong |
| 2024/0016917 | A1 | 1/2024 | Ma et al. |
| 2024/0066113 | A1 | 2/2024 | Wong et al. |
| 2024/0100147 | A1 | 3/2024 | Wong et al. |

FOREIGN PATENT DOCUMENTS

| | | |
|---|---|---|
| CN | 105934441 A | 9/2016 |
| CN | 112626124 A | 4/2021 |
| EP | 1987068 A1 | 11/2008 |
| EP | 2949665 A1 | 12/2015 |
| JP | 2017518989 A | 7/2017 |
| RU | 2720614 C1 | 5/2020 |
| RU | 2730897 C1 | 8/2020 |
| WO | 2007008918 A2 | 1/2007 |
| WO | 2007095506 A1 | 8/2007 |
| WO | 2009002516 A1 | 12/2008 |
| WO | 2009007427 A2 | 1/2009 |
| WO | 2010022737 A1 | 3/2010 |
| WO | 2010111687 A2 | 9/2010 |
| WO | 2010148511 A1 | 12/2010 |
| WO | 2012054907 A2 | 4/2012 |
| WO | 2012088428 A1 | 6/2012 |
| WO | 2013043729 A1 | 3/2013 |
| WO | 2013067652 A1 | 5/2013 |
| WO | 2014115797 A1 | 7/2014 |
| WO | WO-2015057942 A1 * | 4/2015 ............ A61K 39/42 |

(Continued)

OTHER PUBLICATIONS

Magazine et al., Viruses. Mar. 19, 2022;14(3):640. doi: 10.3390/v14030640. PMID: 35337047 PMCID: PMC8949778.*
Focosi et al., Rev Med Virol. Nov. 2021;31(6):e2231. doi: 10.1002/rmv.2231. Epub Mar. 16, 2021. PMID: 33724631 PMCID: PMC8250244.*
Zhang, Xiaojian et al., "Role of stem glycans attached haemagglutinin in the biological characteristics of H5N1 avian influenza virus", Journal of General Virology, 96, 1248-1257, 2015.
Zhang, Yan et al., "Glycosylation on Hemagglutinin Affects the Virulence and Pathogenicity of Pandemic H1N1/2009 Influenza A Virus in Mice", PLOS One, vol. 8, Issue 4, Apr. 2013.
Zhao, "Glycans of SARS-CoV-2 Spike Protein in Virus Infection and Antibody Production", Frontiers in Molecular Biosciences, Apr. 13, 2021; Entire Document; DOI: 10.3389/fmolb.2021.629873.

(Continued)

*Primary Examiner* — Michael Szperka
(74) *Attorney, Agent, or Firm* — Prosyla Group PC

(57) ABSTRACT

The present disclosure relates to an antibody or antigen-binding fragment thereof that specifically binds to a spike protein of SARS-CoV-2. The present disclosure also relates to a pharmaceutical composition, a method for treating and/or preventing diseases and/or disorders caused by a coronavirus in a subject in need thereof, and a method for detecting a coronavirus in a sample.

12 Claims, 12 Drawing Sheets
(1 of 12 Drawing Sheet(s) Filed in Color)
Specification includes a Sequence Listing.

(56) References Cited

FOREIGN PATENT DOCUMENTS

| WO | 2015073727 | A1 | 5/2015 | | |
|---|---|---|---|---|---|
| WO | 2015184004 | A1 | 12/2015 | | |
| WO | 2017062496 | A2 | 4/2017 | | |
| WO | WO2017081082 | A2 | 5/2017 | | |
| WO | 2018089407 | | 11/2017 | | |
| WO | 2019028190 | A1 | 2/2019 | | |
| WO | 2015028478 | A1 | 6/2019 | | |
| WO | 2019246363 | A1 | 12/2019 | | |
| WO | 2020011275 | A1 | 1/2020 | | |
| WO | 2019246363 | | 4/2020 | | |
| WO | 2020172072 | A1 | 8/2020 | | |
| WO | 2020198865 | A1 | 10/2020 | | |
| WO | WO2020205034 | A1 | 10/2020 | | |
| WO | 2021019102 | A2 | 2/2021 | | |
| WO | 2021045836 | A1 | 3/2021 | | |
| WO | 2021180602 | A1 | 9/2021 | | |
| WO | 2021183195 | A1 | 9/2021 | | |
| WO | WO-2021174128 | A1 | * | 9/2021 | ............. A61K 39/12 |
| WO | 2021226533 | A1 | 11/2021 | | |
| WO | WO-2021219897 | A1 | * | 11/2021 | ............. A61K 39/12 |
| WO | 2022221835 | | 4/2022 | | |
| WO | 2022221835 | A2 | 10/2022 | | |
| WO | 2022221837 | A2 | 10/2022 | | |
| WO | PCTUS2282428 | | 12/2022 | | |
| WO | 2023056482 | A1 | 4/2023 | | |
| WO | 2023129928 | A2 | 7/2023 | | |

OTHER PUBLICATIONS

Zheng, J. et al., "Identification of N-linked glycosylation sites in the spike protein and their functional impact on the replication and infectivity of coronavirus infectious bronchitis virus in cell culture", Virology, Oct. 13, 2017, vol. 513, pp. 65-74; abstract; p. 65, 1st column, second paragraph; p. 66, col. 5th paragraph; p. 68, first column, first, third paragraphs; Table 3; figure 5; http://dx.doi.org/10.1016/j.virol.2017.10.003.
U.S. Appl. No. 17/598,064, filed Sep. 24, 2021, Chi-Huey Wong.
U.S. Appl. No. 17/937,744, filed Oct. 3, 2022, Kuo-I Lin.
U.S. Appl. No. 17/998,208, filed Nov. 8, 2022, Chi-Huey Wong.
U.S. Appl. No. 18/005,573, filed Jan. 13, 2023, Che Ma.
U.S. Appl. No. 18/029,758, filed Mar. 31, 2023, Chi-Huey Wong.
U.S. Appl. No. 18/146,873, filed Dec. 27, 2022, Kuo-I Lin.
U.S. Appl. No. 18/501,578, filed Nov. 3, 2023, Chi-Huey Wong.
U.S. Appl. No. 63/266,008, filed Dec. 27, 2021, Kuo-I Lin.
U.S. Appl. No. 63/458,102, filed Apr. 8, 2023, Chi-Huey Wong.
U.S. Appl. No. 63/581,389, filed Sep. 8, 2023, Chi-Huey Wong.
Bosch, Berend Jan et al., "Coronavirus Escape from Heptad Repeat 2 (HR2)-Derived Peptide Entry Inhibition as a Result of Mutations in the HR1 Domain of the Spike Fusion Protein," J of Virol., Mar. 2008, vol. 82, No. 5, pp. 2580-2585.
Cao, Yiwei et al., "Dynamic Interactions of Fully Glycosylated SARS-CoV-2 Spike Protein with Various Antibodies," JCTC, Sep. 16, 2021, vol. 17, pp. 6559-6569.
Castrucci, M.R. et al., "Biologic importance of neuramindase stalk length in influenza A virus", Journal of Virology, 1993, vol. 67, No. 2, pp. 759-764.
Chokhawala, H.A. et al., "Enzymatic Synthesis of Fluorinated Mechanistic Proves for Sialidases and Sialyltransferases", J.Am. Chem. Soc., 2007, p. 10630; scheme 1.
Dang, Juanjuan et al., "Multivalency-assisted membrane-penetrating siRNA delivery sensitizes photothermal ablation via inhibition of tumor glycolysis metabolism," Biomaterials, vol. 223, Dec. 2019, 119463.
Dowling, W. et al., "Influences of Glycosylation on Antigenicity, Immunogenicity, and Protective Efficacy of Ebola Virus GP DNA Vaccines", J. of Virology, 2007, vol. 81, No. 4, pp. 1821-1837, p. 1822, second column, fourth paragraph; p. 1823, second column, third paragraph; doi:10.1128/JVI.02098-06.
Edwards, et al., "The Remarkable Flexibility of the Human Antibody Repertoire; Isolation of Over One Thousand Different Antibodies to a Single Protein, BLyS," J. Mol. Biol., Nov. 2003, 14:334(1):103-18; doi: 10.1016/jmb.2003.09.054. PMID 14596803.
Feng et al., "A Glycolipid Adjuvant, 7DW8-5, Enhances the Protective Immune Response to the Current Slpit Influenza Vaccine in Mice", Frontiers in Microbiology, Sep. 18, 2019, vol. 10, No. 2157M, pp. 1-9; abstract.
Galili, "Amplifying immunogenicity of prospective Covid-19 vaccines by glycoengineering the coronavirus glycan-shield to present alpha-gal epitopes", Vaccine, Aug. 19, 2020; abstract; Fig. 1; DOI: 10.1016/j.vaccine.2020.08.032.
Galili, Uri, "Amplifying immunogenicity of prospective Covid-19 vaccines by glycoengineering the coronavirus glycan-shield to present [alpha]-gal epitopes," Vaccine, 2020, vol. 38, pp. 6487-6499.
GenBank Accession BCN86353.1 accessed on Jan. 22, 2021. https://www.ncbi.nlm.nih.gov/protein/BCN86353.1?report=genbank&log$=protalign&blast_rank=2&RID=EYKWWEAA016.
GenBank Accession CCH23214, haemagglutinin [Influenza A virus (A/WVSN/1933(H1N1))], 2013.
GenBank Accession, ACF54601, neuraminidase [Influenza A virus (A/WSN/1933(H1N1))], 2008.
GenBank: QLB39105.1 accessed on Jan. 1, 2020. https://www.ncbi.nlm.nih.gov/protein/QLB39105.1?report=genbank&log$=protalign&blast_rank=1&RID=EYKWWEAA016.
GenBank: QTA38985.1 accessed Mar. 21, 2021. https://www.ncbi.nlm.nih.gov/protein/QTA38985.1?report=genbank&log$=protalign&blast_rank=3&RID=EYKWWEAA016.
Gillian, M. Air, "Influenza neuraminidase", Influenza and Other Respiratory Viruses, 2011.
Goel, Manisha et al., "Plasticity within the Antigen-Combining Site May Manifest as Molecular Mimicry in the Humoral Immune Response," J. Immunol., Dec. 15, 2004, 173(12):7358-67 PMID: 15585860 DOI: 10.4049/jimmunol.173.12.7358.
Hayashi, T. et al., "Stereospecific α-Sialylation by SIte-Selective Fluorination", Agnew. Chem. Int. Ed., Jan. 25, 2019, vol. 58, pp. 3814-3818. (Whole Document).
Hughes et al., "Adaptation of Influenza A Viruses to Cells Expressing Low Levels of Sialic Acid Leads to Loss of Neuraminidase Activity", Journal of Virology, 2001, vol. 75, No. 8, pp. 3766-3770.
International Search Report and Written Opinion issued on Jun. 22, 2023 in International Patent Application No. PCT/US22/82428.
Janeway Jr., Charles A et al., "Immunobiology: The Immune System in Health and Disease," 3rd edition, Garland Publishing Inc., 1997, pp. 3:1-3:11.
Kanyavuz, Alexia et al., "Breaking the law: unconventional strategies for antibody diversification," Nat Rev Immunol., Jun. 2019, 19(6):355-368. doi:10.1038/S41577-019-0126-7. PMID: 30718829.
Lescar et al., "Crystal Structure of a Cross-reaction Complex between Fab F9.13.7 and Guinea Fowl Lysozyme," J Biol Chem., Jul. 1995, 270(30):18067-76. doi: 10.1074/jbc.270.30.18067. PMID: 7629116.
Li, et al., Glycosylation of Neuraminidase Determines the Neurovirulence of Influenza A/WSN/33 Virus, 1993, Journal of Virology, vol. 67, No. 11, pp. 6667-6673.
Liu, Wen-Chun et al., "Unmasking Stem-Specific Neutralizing Epitopes by Abolishing N-Linked Glycosylation Sites of Influenza Virus Hemagglutinin Proteins for Vaccine Design", Journal of Virology, vol. 90 No. 19, Oct. 2016.
Lloyd, C. et al., "Modelling the human immune response: performance of a 10(11) human antibody repertoire against a broad panel of therapeutically relevant antigens," Protein Engineering Design & Selection, 2009, vol. 22, No. 3, pp. 159-168. doi: 10.1093/protein/gzn058.
Lo, H.-J. et al., "Synthesis of Sialidase-Resistant Oligosaccharide and Antibody Glycoform Containing α2,6-Linked 3Fax-Neu5Ac", J. Am. Chem. Soc., Apr. 10, 2019, vol. 141, No. 16, pp. 6484-6488. (Whole Document.).
Lostalé-Seijo, Irene and Montenegro, Javier, "Synthetic materials at the forefront of gene delivery," Nature Reviews Chemistry, vol. 2, Sep. 21, 2018, pp. 258-277.

(56) References Cited

OTHER PUBLICATIONS

Medina, Rafael A. et al., "Glycosylations in the globular head of the hemagglutinin protein modulate the virulence and antigenic properties of the H1N1 influenza viruses", Sci Transl Med., May 29, 2013.
Nobusawa et al., "Comparison of Complete Amino Acid Sequences and Receptor-Binding Properties among 13 Serotypes of Hemagglutinins of Influenza A Viruses", Virology, 182, 475-485 (1991).
Non-Final Office Action issued in U.S. Appl. No. 17/937,744 dated Jul. 5, 2023.
Office Action issued in Taiwan Patent Application No. 111113932 on Oct. 16, 2023.
Office Action issued on Nov. 14, 2022, in Israel Patent Application No. 293502.
Official Action, dated Aug. 31, 2023, received in Russia Patent Application No. 2023100504. English translation provided.
Okamoto, K. et al., "An effective synthesis of α-glycosides of N-acetylneuraminic acid by use of 2β-halo-3β-hydroxy-4,7,8,9-tetra-O-acetyl-N-acetylneuraminic acid methyl ester", Tetrahedron Letters, 1986, vol. 27, No. 43, pp. 5233-5236.
Rahman, M Shaminur et al., "Epitope-based chimeric peptide vaccine design against S, M, and E proteins of SARS-CoV-2, the etiologic agent of COVID-19 pandemic, an in silico approach", PeerJ, Jul. 27, 2020 (publication date), DOI 10.7717/peerj.9572, Internal pp. 1-30, Supplemental Information pp. 1, 2. Abstract; and supplemental information pp. 1, 2.
Rees-Spear, Chloe et al., "The effect of spike mutations on SARS-CoV-2 neutralization," Cell Rep., Mar. 2023, 34(12): 108890. Published online Mar. 6, 2021. doi: 10.1016/j.celrep.2021.108890: 10.1016/j.celrep.2021.108890 PMCID: PMC7936541 PMID: 33713594.
Roberts, Paul C. et al., "Role of Conserved Glycosylation Sites in Maturation and Transport of Influenza A Virus Hemagglutinin", Journal of Virology, Jun. 1993, p. 3048-3060.
Rudikoff et al., "Single amino acid substitution altering antigen-binding specificity," Proc. Natl Acad Sci U S A, Mar. 1982, vol. 79(6), pp. 1979-1983. doi: 10.1073/pnas.79.6.1979. PC/D: 6804947.
Sanda, Miloslav et al., "N- and O-Glycosylation of the SARS-CoV-2 Spike Protein," Anal. Chem., vol. 93, No. 4, Jan. 7, 2021, pp. 2003-2009.
Search Report, dated Aug. 31, 2023, received in Russia Patent Application No. 2023100504.
Sun et al., "N-Linked Glycosylation of the Hemagglutinin Protein Influences Virulence and Antigenicity of the 1918 Pandemic and Seasonal H1N1 Influenza A Viruses", 2013, Journal of Virology, vol. 87, No. 15, pp. 8756-8766.
Tai, Wanbo et al., "Characterization of the receptor-binding domain (RBD) of 2019 novel coronavirus: implication for development of RBD protein as a viral attachment inhibitor and vaccine," Cell Mol Immunol. Jun. 2020; 17(6):613-620 https://pubmed.ncbi.nlm.nih.gov/32203189/.
Tian, Jing-Hui et al., "SARS-CoV-2 spike glycoprotein vaccine candidate NVX-CoV2373 immunogenicity in baboons and protection in mice," Nature Communications, 2021, 14 pages. Downloaded Sep. 27, 2023: https://doi.org/10.1038/s41467-020-20653-8.
Torres-Vanegas, Julian D., "Delivery Systems for Nucleic Acids and Proteins: Barriers, Cell Capture Pathways and Nanocarriers," Pharmaceutics, vol. 13, No. 3, Mar. 22, 2021, pp. 428.
Vogel, Annette B. et al. "BNT162b vaccines protect rhesus macaques from SARS-CoV-2," Nature, vol. 592, Feb. 1, 2021, pp. 283-289.
Weissman, Drew et al., "D614G Spike Mutation Increases SARS CoV-2 Susceptibility to Neutralization," Cell Host & Microbe, Jan. 13, 2021, vol. 29, pp. 23-31 (e1-e4).
Wu, Chung-Yi et al., "Influenza A surface glycosylation and vaccine design", PNAS, Jan. 2017, (Epub Dec. 27, 2016), vol. 114, No. 2, pp. 280-285.
Yang, Zhiwei et al., "Mutation effects of neuraminidases and their docking with ligands: a molecular dynamics and free energy calculation study", J Comput Aided Mol Des, 27: 935-950, 2013.
Zaraket, Hassan et al., "Full Genome Characterization of Human Influenza A/H3N2 Isolates from Asian Countries Reveals a Rare Amantadine Resistance-Conferring Mutation and Novel PB1-F2 Polymorphisms", Frontiers in Microbiology, vol. 7, Article 262, Mar. 2016.
U.S. Appl. No. 63/549,343, filed Feb. 2, 2024, Chi-Huey Wong.
U.S. Appl. No. 63/588,932, filed Oct. 9, 2023, Chi-Huey Wong.
Davies, Nicholas G. et al., "Estimated transmissibility and impact of SARS-CoV-2 lineage B.1.1.7 in England," Science, Apr. 2021, vol. 372, pp. 149 (10 pages).
GenBank accession MN908947.3, Mar. 18, 2020, 11 pages. (https://www.ncbi.nlm.nih.gov/nuccore/MN908947).
Office Action and Search Report issued in Taiwan Patent Application No. 111113933 on Mar. 26, 2024. English translation of search report.
Watanabe, Yasunori et al., "Site-specific glycan analysis of the SARS-CoV-2 spike," Science, Jul. 2020, vol. 369, pp. 330-333.
Bernstein, David et al., "Immunogenicity of chimeric haemagglutinin-based, universal influenza virus vaccine candidates: interim results of a randomized, placebo-controlled, phase 1 clinical trial", The Lancet Infectious Disease, Elsevier, Amerstdam, NL, vol. 20, No. 1, Oct. 17, 2019, pp. 80-91, XP085982810. ISSN: 1473-3099, DOI: 10.1016/S1473-3099(19)30393-7.
Huang et al., "Impact of glycosylation on SARS-CoV-2 infection and broadly protective vaccine design," BioRxiv, May 25, 2021, DOI: https://doi.org/10.1101/2021.05.25.445523, internal pp. 1-48.

\* cited by examiner

ANTIBODY SPECIFIC TO SPIKE PROTEIN OF SARS-CoV-2 AND USES THEREOF

PRIORITY INFORMATION

The present application is a continuation of U.S. patent application Ser. No. 17/937,744, filed Oct. 3, 2022, which claims priority to and benefit of U.S. Provisional Patent Application No. 63/251,472, filed Oct. 1, 2021, the disclosure of which is incorporated in its entirety herein.

SEQUENCE LISTING

The instant application contains a Sequence Listing which is submitted electronically in .xml format and is hereby incorporated by reference in its entirety. The .xml copy, created on Jan. 11, 2024, is named "A1000-00800C_CorrectedSeqListing_20240111" and is 10 kilobytes in size.

FIELD OF THE DISCLOSURE

The present disclosure relates to an antibody or antigen-binding fragment thereof, which is specific to a spike protein of SARS-CoV-2, and uses thereof.

BACKGROUND OF THE DISCLOSURE

The COVID-19 pandemic caused by the severe acute respiratory syndrome coronavirus 2 (SARS-CoV-2) has spread globally. The infection causes symptoms of direct cytopathic effects and excessive inflammatory responses in the infected subject. The lack of valid treatment causes high morbidity and mortality. The emergence of these newly identified viruses highlights the need for the development of novel antiviral strategies.

Thus, there is need for development of an effective treatment for COVID-19.

SUMMARY OF THE DISCLOSURE

The present disclosure provides novel neutralizing therapeutic anti-Coronavirus spike protein (such as anti-SARS-CoV-2-Spike protein) antibodies and their use for treating or preventing viral infection.

Accordingly, the present disclosure provides an antibody or antigen-binding fragment thereof that is specific for an epitope in a spike protein of coronaviruses (CoVs), particularly, SARS-CoV-2. The antibody according to the disclosure is thus useful for treating and/or preventing diseases and/or disorders caused by or related to CoVs, particularly SARS-CoV-2. The antibody of the disclosure is also useful for detecting CoVs (particularly, SARS-CoV-2).

The present disclosure also provides an epitope comprises a part locating in 419 to 433 amino acid residues or 471 to 482 amino acid residues of SEQ ID NO: 8. In some embodiments, the epitope comprises a part locating in 419 to 433 amino acid residues and 471 to 482 amino acid residues of SEQ ID NO: 8. Accordingly, the present disclosure provides an antibody binding to the epitope disclosed herein.

In some embodiments, the disclosure provides an antibody or antigen-binding fragment thereof that specifically binds to an epitope in a spike protein of a CoV; wherein the antibody or antigen-binding fragment thereof comprises complementarity determining regions (CDRs) of a heavy chain variable region and complementarity determining regions of a light chain variable region, wherein the complementarity determining regions of the heavy chain variable region comprise CDRH1, CDRH2, and CDRH3 regions, and the complementarity determining regions of the light chain variable region comprise CDRL1, CDRL2, and CDRL3 regions, and wherein:
the CDRH1 region comprises the amino acid sequence of GYTFTEYT (SEQ ID NO: 1) or a substantially similar sequence thereof; the CDRH2 region comprises the amino acid sequence of INPNIGDT (SEQ ID NO: 2) or a substantially similar sequence thereof; the CDRH3 region comprises the amino acid sequence of AREVYNYSFAY (SEQ ID NO: 3) or a substantially similar sequence thereof; and
the CDRL1 region comprises the amino acid sequence of QSLLYSSNQKNY (SEQ ID NO: 4) or a substantially similar sequence thereof; the CDRL2 region comprises the amino acid sequence of WAS or a substantially similar sequence thereof; the CDRL3 region comprises the amino acid sequence of QQYYRYPLT (SEQ ID NO: 5) or a substantially similar sequence thereof.

In some embodiments of the disclosure, the spike protein is fully glycosylated. In one embodiment, the spike protein is monoglycosylated.

In some embodiments of the disclosure, the antibody or antigen-binding fragment thereof comprises a heavy chain variable region comprising the amino acid sequence of MGWSLILLFLVAVATRVEVQLQQSGPEMVKP-GASVKISCKTSGYTFTEYTIYWVKQSH GKSLEWLG-GINPNIGDT-
TYNQKFKGKATLTVDTSSSTAYMELRSLTSEDSAVYY-CARE
VYNYSFAYWGQGTLVTVSAASTKGPSVF-PLAPSSKSTSGGTAALGCLVKDYFPEPVTV
SWNSGALTSGVHTFPAVLQSSGLYS-LSSVVTVPSSSLGTQTYICNVNHKPSNTKVDKK
AEPKSCDKTHTCPPCPA-
PELLGGPSVFLFPPKPKDTLMISRTPE-
VTCVVVDVSHEDPEV
KFNWYVDGVEVHNAKTKPREEQYN-
STYRVVSVLTVLHQDWLNGKDYKCKVSNKA LPA-PIEKTISKAKGQPREPQVYTLPPSRDELTRNQVSLT-CLVKGFYPSDIAVEWESNGQP
ENNYKTTPPVLDSDGSFFLYSK-
LTVDKSRWQQGNVFSCSVMHEALHNHYTQKSLSLS PGK (SEQ ID NO: 6) or a substantially similar sequence thereof; and a light chain variable region comprising the of amino acid sequence MRVPAQLLGLLLLWLPGARCDI-VMSQSPSSLAVSVGEKVTMSCKSSQSLLYSSNQKN
YLAWYQQKLGQTPKLLIYWAS-
SRESGVPDRFTGSGSGTDFTLTISSVRAEDLAVYYCQ
QYYRYPLTFGVGTKLELKRTVAAPSVFIFPPSD-
EQLKSGTASVVCLLNNFYPREAKVQ WKVD-NALQSGNSQESVTEQDSKDSTYSLSSTLTL-
SKADYEKHKVYACEVTHQGLSSP VTKSFNRGEC (SEQ ID NO: 7) or a substantially similar sequence thereof.

In some embodiments of the disclosure, the antibody is a monoclonal antibody, chimeric antibody, humanized antibody or human antibody.

In some embodiments of the disclosure, the antibody is multispecific.

The present disclosure also provides a complex comprising the antibody or antigen-binding fragment thereof as disclosed herein bound to a spike protein of a CoV or fragments thereof.

The present disclosure provides a vector encoding the antibody or antigen-binding fragment thereof as disclosed herein.

The present disclosure provides a genetically engineered cell expressing the antibody or antigen-binding fragment thereof as disclosed herein or containing the vector as disclosed herein.

The present disclosure also provides a method for manufacturing the antibody or antigen-binding fragment thereof as disclosed herein, comprising: (a) introducing into a host cell one or more polynucleotides encoding said antibody or antigen-binding fragment; (b) culturing the host cell under conditions favorable to expression of the one or more polynucleotides; and (c) optionally, isolating the antibody or antigen-binding fragment from the host cell and/or a medium in which the host cell is grown.

The present disclosure provides a pharmaceutical composition comprising the antibody or antigen-binding fragment thereof as disclosed herein and pharmaceutically acceptable carrier and, optionally, a further therapeutic agent.

Examples of the therapeutic agent include but are not limited to an antiviral agent. In some embodiments of the disclosure, the therapeutic agent is an anti-inflammatory agent or an antibody or antigen-binding fragment thereof that specifically binds to a spike protein of a CoV.

In some embodiments of the disclosure, the subject is vaccinated.

The present disclosure provides a vessel or injection device comprising the antibody or antigen-binding fragment thereof as disclosed herein.

The present disclosure provides use of the antibody or antigen-binding fragment thereof as described herein in the manufacture of a medicament for treating or preventing infection with a coronavirus in a subject in need thereof. Alternatively, the present disclosure provides a method for treating or preventing infection with a coronavirus in a subject in need thereof, comprising administering a therapeutically effective amount of the antibody or antigen-binding fragment thereof as disclosed herein.

In some embodiments of the disclosure, the CoV described herein is alpha-CoV, beta-CoV, gamma-CoV, and delta-CoV2. In some embodiments, the CoV described herein includes, but is not limited to, SARS-CoV, MERS-CoV or SARS-CoV-2.

In some embodiments of the disclosure, the medicament is adminstered with one or more further therapeutic agents. Alternatively, the subject is administered one or more further therapeutic agents.

The present disclosure provides a method for neutralizing a coronavirus in a subject in need thereof, comprises administering to the subject the antibody or antigen-binding fragment thereof as disclosed herein.

The present disclosure provides a method for administering the antibody or antigen-binding fragment thereof as disclosed herein into the body of a subject comprising injecting the antibody or antigen-binding fragment into the body of the subject.

In some embodiments of the disclosure, the medicament is injected into the body of the subject subcutaneously, intravenously, or intramuscularly. Alternatively, the antibody or antigen-binding fragment is injected into the body of the subject subcutaneously, intravenously, or intramuscularly.

The present disclosure provides a method for detecting a coronavirus in a sample comprising contacting the sample with the antibody or antigen-binding fragment thereof as disclosed herein.

The present disclosure provides a kit for detecting a coronavirus in a sample, wherein the kit comprises the antibody or antigen-binding fragment thereof as disclosed herein.

The present disclosure is described in detail in the following sections. Other characteristics, purposes and advantages of the present disclosure can be found in the detailed description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows overview of the single B cell screening platform. Single spike-specific B cells (CD3$^-$CD19$^+$spike$^+$) from spleen of immunized mice were sorted into 96-well plates by FACS. The IgH and IgL gene transcripts of each single B cell were amplified by RT-PCR. After sequencing, the cDNAs from the variable regions of IgH or IgL genes were subcloned into the expression vectors containing human Ig heavy chain or light chain constant region, respectively. The chimeric monoclonal antibody was produced by Expi 293, and its binding to spike protein was measured by using spike-expressing 293T cells and FACS. FIG. 1B shows the heavy distribution of the B cell repertoire. Less than 5% usage is shown in white. FIG. 1C shows that analysis of heavy chain IgG repertoires of $S_{fg}$ or $S_{mg}$ immunized mice showed highly-represented IGHV1-9, IGHV1-18 and IGHV2-3 in the $S_{mg}$ group (p-values: 0.048, 1.6×10$^{-11}$ and 0.005, respectively, by using Chi-squared test).

FIG. 2A shows ELISA binding of m31A7 to S1, S2, RBD or the S protein. FIG. 2B shows FACS analysis of m31A7 binding to HEK293T cells expressing S protein of SARS-CoV-2 WT and variants (including D614G, B.1.1.7 [alpha], B.1.351 [beta], and B.1.617.2 [delta]).

FIG. 3A shows neutralization of m31A7 against SARS-CoV-2 WT and variants pseudoviruses. FIG. 3B shows pseudovirus microneutralization of SARS-CoV-2 WT and variants by m31A7 in comparison with previously reported mAb EY6A (grey). Variant species (including D614G, B.1.1.7 [alpha], B.1.351[beta], and B.1.617.2 [delta]) are labeled on top of each panel.

FIG. 4A shows antibody injection and challenge schedule by using K18hACE2 transgenic mice. FIG. 4B shows weight changes after SARS-CoV-2 infection in PBS or m31A7 treated mice. FIG. 4C shows body temperature changes after SARS-CoV-2 infection in PBS or m31A7 treated mice. *P<0.05.

FIG. 5A shows dissociation constants of m31A7 IgG and Fab to S protein. FIG. 5B shows dissociation constants of m31A7 IgG and Fab to BA.1 S protein. FIG. 5C shows epitope mapping of RBD by HDX-MS showing potential m31A7-binding peptides, measured at 15 sec. FIG. 5D shows volcano plots of the changes in deuterium uptake in RBD upon addition of m31A7 IgG, with the hits (ΔHDX>5%, q value<0.01) shown in the top right corner and highlighted in red. Unlabeled hits are redundant peptides with 471-482. *P<0.05; P<0.01; *P<0.001.

DETAILED DESCRIPTION OF THE DISCLOSURE

Figure 1A:
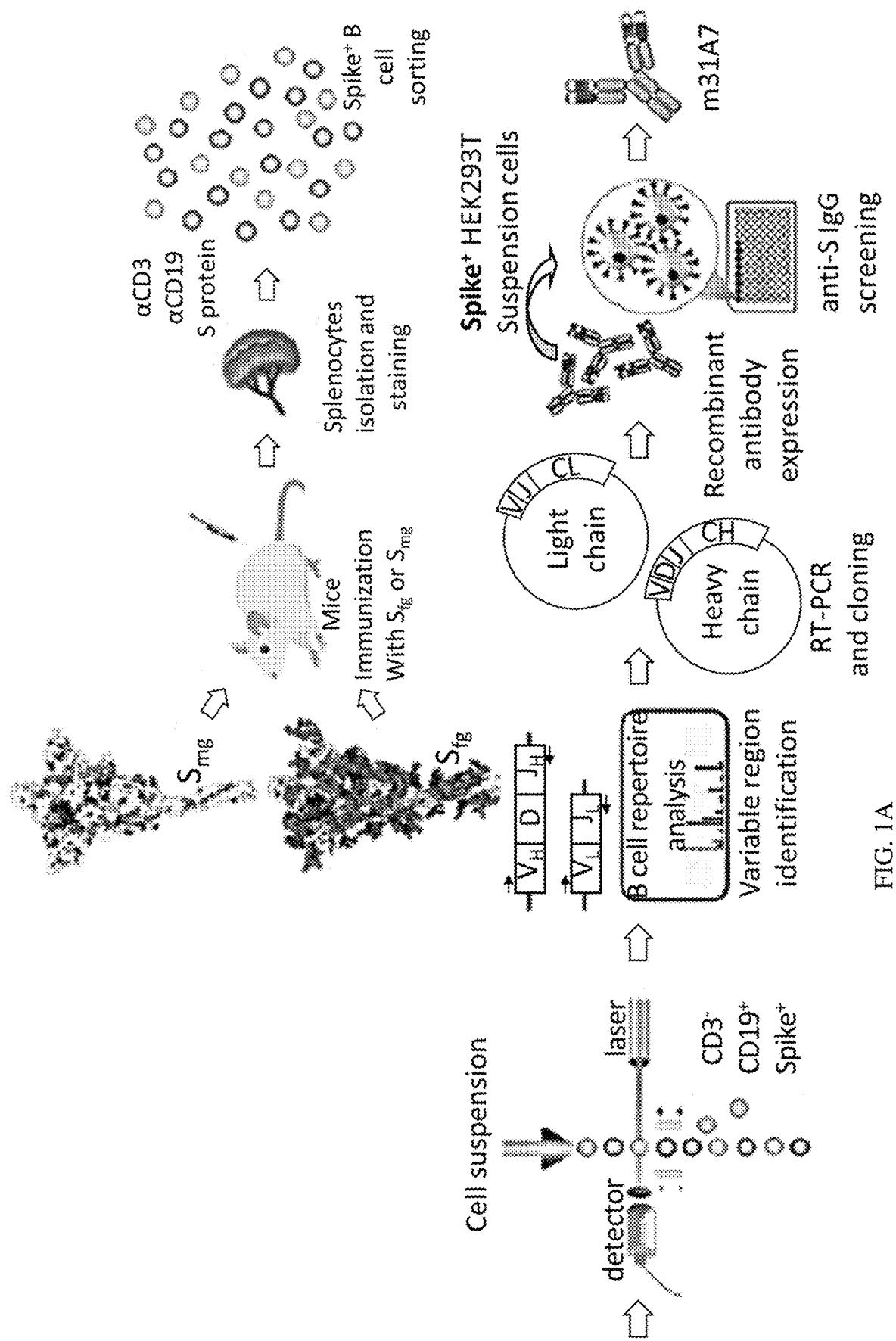
FIGS. 1A to 1C show identification of m31A7 mAb from $S_{mg}$ immunized mice and the comparison of heavy chain of spike specific B cell repertoires elicited by $S_{mg}$ and $S_{fg}$.

It is understood that this invention is not limited to the particular materials and methods described herein. It is also to be understood that the terminology used herein is for the purpose of describing particular embodiments and is not intended to limit the scope of the present invention, which will be limited only by the appended claims.

It must be noted that, as used in this specification and the appended claims, the singular forms "a," "an," and "the" include plural referents unless the content clearly dictates otherwise.

The term "antibody", as used herein, refers to any antigen-binding molecule or molecular complex comprising at least one complementarity determining region (CDR) that specifically binds to or interacts with a particular antigen (SARS-CoV-2-Spike protein). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-SARS-CoV-2-Spike protein antibody (or antigen-binding portion thereof) may be identical to the human germline sequences, or may be naturally or artificially modified. An amino acid consensus sequence may be defined based on a side-by-side analysis of two or more CDRs.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex.

As used herein, the term "specifically binds" means that an antibody does not cross react to a significant extent with other epitopes.

As used herein, the term "epitope" refers to the site on the antigen to which an antibody binds.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains; phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

The term "monoclonal antibody" as used herein is not limited to antibodies produced through hybridoma technology. A monoclonal antibody is derived from a single clone, including any eukaryotic, prokaryotic, or phage clone, by any refers to available or known in the art.

The term "chimeric" antibody as used herein refers to an antibody having variable sequences derived from a non-human immunoglobulin and human immunoglobulin constant regions, typically chosen from a human immunoglobulin template.

"Humanized" forms of non-human antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence.

As used in the present disclosure, the term "fully glycosylated" refers to a state of glycosylation on a CoV spike protein (particular, SARS-CoV-2-Spike protein) wherein all N-glycan sites within the CoV spike protein (particular, SARS-CoV-2-Spike protein) are glycosylated with at least one sugar moiety.

As used in the present disclosure, the term "therapeutic agent" refers to any compound, substance, drug, drug or active ingredient having a therapeutic or pharmacological effect that is suitable for administration to a mammal, for example a human.

As used herein, the term "immunoconjugate" refers to an antigen-binding protein, e.g., an antibody or antigen-binding fragment, which is chemically or biologically linked to a radioactive agent, a cytokine, an interferon, a target or reporter moiety, an enzyme, a peptide or protein or a therapeutic agent. The antigen-binding protein may be linked to the radioactive agent, cytokine, interferon, target or reporter moiety, enzyme, peptide or therapeutic agent at any location along the molecule so long as it is able to bind its target (CoV-S). Examples of immunoconjugates include antibody-drug conjugates and antibody-toxin fusion proteins. In one embodiment of the invention, the agent may be a second, different antibody that binds specifically to CoV-S. The type of therapeutic moiety that may be conjugated to the anti-CoV-S antigen-binding protein (e.g., antibody or fragment) will take into account the condition to be treated and the desired therapeutic effect to be achieved.

As used herein, the term "vector" is intended to refer to a nucleic acid molecule capable of transporting another nucleic acid to which it has been linked.

The term "genetically engineered" or "genetic engineering" of cells refers to manipulating genes using genetic materials for the change of gene copies and/or gene expression level in the cell. The genetic materials can be in the form of DNA or RNA. The genetic materials can be transferred into cells by various means including viral transduction and non-viral transfection. After being genetically engineered, the expression level of certain genes in the cells can be altered permanently or temporarily.

The term "coronavirus" or "CoV" refers to any virus of the coronavirus family, including but not limited to SARS-CoV-2, MERS-CoV, and SARS-CoV. SARS-CoV-2 refers to the newly-emerged coronavirus which is rapidly spreading to other areas of the globe. It binds via the viral spike protein to human host cell receptor angiotensin-converting enzyme 2 (ACE2). The spike protein also binds to and is cleaved by TMPRSS2, which activates the spike protein for membrane fusion of the virus.

The term "CoV-S", also called "S" or "S protein" refers to the spike protein of a coronavirus, and can refer to specific S proteins such as SARS-CoV-2-S, MERS-CoV S, and SARS-CoV S.

The term "coronavirus infection" or "CoV infection," as used herein, refers to infection with a coronavirus such as SARS-CoV-2, MERS-CoV, or SARS-CoV. The term includes coronavirus respiratory tract infections, often in the lower respiratory tract. Symptoms can include high fever, dry cough, shortness of breath, pneumonia, gastro-intestinal symptoms such as diarrhea, organ failure (kidney failure and renal dysfunction), septic shock, and death in severe cases.

As used in the present invention, the term "pharmaceutical composition" refers to a mixture containing a therapeutic agent administered to a mammal, for example a human, for preventing, treating, or eliminating a particular disease or pathological condition that the mammal suffers.

As used herein, the term "therapeutically effective amount" or "efficacious amount" refers to the amount of an antibody that, when administered to a mammal or other subject for treating a disease, is sufficient to affect such treatment for the disease.

As used herein, the terms "treatment," "treating," and the like, cover any treatment of a disease in a mammal, particularly in a human, and include: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The term "preventing" or "prevention" is recognized in the art, and when used in relation to a condition, it includes administering, prior to onset of the condition, an agent to reduce the frequency or severity of or to delay the onset of symptoms of a medical condition in a subject, relative to a subject which does not receive the agent.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc. Particularly, the subject is vaccinated.

As used herein, the term "in need of treatment" refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that includes the knowledge that the subject is ill, or will be ill, as the result of a condition that is treatable by the compounds of the present disclosure.

As used herein, the term "sample" encompasses a variety of sample types obtained from an individual, subject or patient and can be used in a diagnostic or monitoring assay. The definition encompasses blood and other liquid samples of biological origin, solid tissue samples such as a biopsy specimen or tissue cultures or cells derived therefrom and the progeny thereof.

A "neutralizing" refers to a process that a molecule (e.g. antibody) inhibits an activity of a coronavirus to any detectable degree, e.g., inhibits the ability of coronavirus to bind to a receptor, to be cleaved by a protease, or to mediate viral entry into a host cell or viral reproduction in a host cell.

Coronaviruses (CoVs) infect human and animals and cause varieties of diseases, including respiratory, enteric, renal, and neurological diseases. CoV uses its spike glycoprotein (S), a main target for neutralization antibody, to bind its receptor, and mediate membrane fusion and virus entry. The coronavirus spike protein is highly conserved among all human coronaviruses (CoVs) and is involved in receptor recognition, viral attachment, and entry into host cells. Similarly, SARS-CoV-2 S protein is also highly conserved with that of CoVs. When the S protein binds to the receptor, TM protease serine 2 (TMPRSS2), a type 2 TM serine protease located on the host cell membrane, promotes virus entry into the cell by activating the S protein. Once the virus enters the cell, the viral RNA is released, polyproteins are translated from the RNA genome, and replication and transcription of the viral RNA genome occur via protein cleavage and assembly of the replicase-transcriptase complex. Viral RNA is replicated, and structural proteins are synthesized, assembled, and packaged in the host cell, after which viral particles are released (Fehr A R, Perlman S. *Coronaviruses: an overview of their replication and pathogenesis. Methods Mol Biol.* 2015; 1282:1-23).

The SARS-CoV-2-Spike protein is a 1273 amino acid type I membrane glycoprotein which assembles into trimers that constitute the spikes or peplomers on the surface of the enveloped coronavirus particle. The protein has two essential functions, host receptor binding and membrane fusion, which are attributed to the N-terminal (S1) and C-terminal (S2) halves of the S protein. CoV-S binds to its cognate receptor via a receptor binding domain (RBD) present in the S1 subunit. The amino acid sequence of full-length SARS-CoV-2 spike protein is exemplified by the amino acid sequence of QCVNLTTRTQLPPAY- TNSFTRGVYYPDKVFRSSVLHSTQDLFLPFF-
SNVTWFHAIHVS
GTNGTKRFDNPVLPFNDGVYFASTEKSNIIRGWIFGT-
TLDSKTQSLLIVNNATNVVIKV CEFQFCNDP-
FLGVYYHKNNKSWMESEFRVYSSANNCTFEYVSQP-
FLMDLEGKQGNF
KNLREFVFKNIDGYFKIYSKHTPINLVRDLPQGF-
SALEPLVDLPIGINITRFQTLLALHRS
YLTPGDSSSGWTAGAAAYYVGYLQPRT-
FLLKYNENGTITDAVDCALDPLSETKCTLK
SFTVEKGIYQTSNFRVQPTESIVRFPNITNLCPF-
GEVFNATRFASVYAWNRKRISNCVAD YSVLYNSASF-
STFKCYGVSPTKLNDLCFTNVYADSFVIR-
GDEVRQIAPGQTGKIADYN
YKLPDDFTGCVIAWNSNNLDSKVGGNYNYLYRL-
FRKSNLKPFERDISTEIYQAGSTPC NGVEGFN-
CYFPLQSYGFQPTNGVGYQPYRVVVLSFELL-
HAPATVCGPKKSTNLVKNK
CVNFNFNGLTGTGVLTESNKKFLPFQQFGRDIADTT-
DAVRDPQTLEILDITPCSFGGVS VITPGTNTSNQVA-
VLYQDVNCTEVPVAIHADQLTPTWRVYSTG-
SNVFQTRAGCLIGAE
HVNNSYECDIPIGAG-
ICASYQTQTNSPGSAGSVASQSIIAYTMSLGAENS-
VAYSNNSIAI PTNFTISVTTEIL-
PVSMTKTSVDCTMYICGDSTECSNLLLQYGSFCT-
QLNRALTGIAVE QDKNTQEVFAQVKQIYKTP-
PIKDFGGFNFSQILPDPSKPSKRSFIEDLLFNKVT-
LADAG FIKQYGDCLGDIAARDLICAQKFNGLTVLP-
PLLTDEMIAQYTSALLAGTITSGWTFGA
GAALQIPFAMQMAYRFNGIGVTQNVLY-
ENQKLIANQFNSAIGKIQDSLSSTASALGKL
QDVVNQNAQALNTLVKQLSSNFGAIS-
SVLNDILSRLDPPEAEVQIDRLITGRLQSLQTY VTQQ-
LIRAAEIRASANLAATKM-
SECVLGQSKRVDFCGKGYHLMSFPQSAPHGVVFLH
VTYVPAQEKNFTTAPAICHDGKAHF-
PREGVFVSNGTHWFVTQRNFYEPQIITTDNTFV
SGNCDVVIGIVNNTVYDPLQPELDSF-
KEELDKYFKNHTSPDVDLGDISGINASVVNIQ
KEIDRLNEVAKNLNESLIDLQEL-
GKYEQDIRSLVPRGSPGSGYIPEAPRDGQAYVRKD
GEWVLLSTFLG (SEQ ID NO: 8). Examples of variants of SARS-CoV-2 spike protein include but are not limited to D614G: D614G; B.1.1.7: 69-70 deletion, 144 deletion, N501Y, A570D, D614G, P681H, T716I, S982A and D1118H; B.1.351: L18F, D80A, D215G, 242-244 deletion, R246I, K417N, E484K, N501Y, D614G and A701V. The term "CoV-S" includes protein variants of CoV spike protein isolated from different CoV isolates as well as recombinant CoV spike protein or a fragment thereof. The term also encompasses CoV spike protein or a fragment thereof coupled to, for example, a histidine tag, mouse or human Fc, or a signal sequence such as ROR1.

The present disclosure surprisingly found an epitope comprising a part locating in 419 to 433 amino acid residues or 471 to 482 amino acid residues of SEQ ID NO: 8. Accordingly, the present disclosure provides an antibody binding to the epitope disclosed herein.

The present disclosure develops an antibody or antigen-binding fragment thereof that is specific for an epitope in a CoV spike protein (particularly, SARS-CoV-2-Spike protein).

Particularly, the antibody or antigen-binding fragment thereof comprises complementarity determining regions (CDRs) of a heavy chain variable region and complementarity determining regions of a light chain variable region, wherein the complementarity determining regions of the heavy chain variable region comprise CDRH1, CDRH2, and CDRH3 regions, and the complementarity determining regions of the light chain variable region comprise CDRL1, CDRL2, and CDRL3 regions, and wherein:

the CDRH1 region comprises the amino acid sequence of SEQ ID NO: 1 or a substantially similar sequence having at least 90%, at least 95%, at least 98% or at least 99% sequence identity; the CDRH2 region comprises the amino acid sequence of SEQ ID NO: 2 or a substantially similar sequence having at least 90%, at least 95%, at least 98% or at least 99% sequence identity; the CDRH3 region comprises the amino acid sequence of SEQ ID NO: 3 or a substantially similar sequence having at least 90%, at least 95%, at least 98% or at least 99% sequence identity; and the CDRL1 region comprises the amino acid sequence of SEQ ID NO: 4 or a substantially similar sequence having at least 90%, at least 95%, at least 98% or at least 99% sequence identity; the CDRL2 region comprises the amino acid sequence of WAS or a substantially similar sequence having at least 90%, at least 95%, at least 98% or at least 99% sequence identity; the CDRL3 region comprises the amino acid sequence of SEQ ID NO: 5 or a substantially similar sequence having at least 90%, at least 95%, at least 98% or at least 99% sequence identity.

In some embodiments of the disclosure, the antibody or antigen-binding fragment thereof is m31A7, comprising the amino acid sequence of SEQ ID NO: 6 or a substantially similar sequence having at least 90%, at least 95%, at least 98% or at least 99% sequence identity; and a light chain variable region comprising the amino acid sequence of SEQ ID NO: 7 or a substantially similar sequence having at least 90%, at least 95%, at least 98% or at least 99% sequence identity; the CDRH1 region comprises the amino acid sequence of SEQ ID NO: 1 or a substantially similar sequence having at least 90%, at least 95%, at least 98% or at least 99% sequence identity; the CDRH2 region comprises the amino acid sequence of SEQ ID NO: 4 or a substantially similar sequence having at least 90%, at least 95%, at least 98% or at least 99% sequence identity.

The antibody according to the disclosure can be full-length (for example, an IgG1 or IgG4 antibody) or may comprise only an antigen-binding portion (for example, a Fab, F(ab')$_2$ or scFv fragment), and may be modified to affect functionality as needed.

In some embodiments of the disclosure, antibody or antigen-binding fragment thereof is conjugated with an anti-CoV-S antigen-binding proteins, e.g., antibodies or antigen-binding fragments, conjugated to another moiety, e.g., a therapeutic moiety (an "immunoconjugate"), such as a toxoid or an antiviral agent to treat coronavirus infection. In an embodiment of the invention, an anti-CoV-S antibody or fragment is conjugated to any of the further therapeutic agents set forth herein.

Various techniques known to persons of ordinary skill in the art can be used to determine whether an antibody "specifically binds to one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody specifically binds is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/ antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267(2):252-259; Engen and Smith (2001) Anal. Chem. 73:256A-265A.

One could easily determine whether an antibody specifically binds to the same epitope as, or competes for binding with, a reference anti-SARS-CoV-2-Spike protein antibody by using routine methods known in the art. For example, to determine if a test antibody binds to the same epitope as a reference anti-SARS-CoV-2-Spike protein antibody of the disclosure, the reference antibody is allowed to bind to a SARS-CoV-2-Spike protein. Next, the ability of a test antibody to bind to the SARS-CoV-2-Spike protein molecule is assessed. If the test antibody is able to bind to SARS-CoV-2-Spike protein following saturation binding with the reference anti-SARS-CoV-2-Spike protein antibody, it can be concluded that the test antibody binds to a different epitope than the reference anti-SARS-CoV-2-Spike protein antibody. On the other hand, if the test antibody is unable to bind to the SARS-CoV-2-Spike protein molecule following saturation binding with the reference anti-SARS-CoV-2-Spike protein antibody, then the test antibody may bind to the same epitope as the epitope bound by the reference anti-SARS-CoV-2-Spike protein antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay. Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

The antibody also includes an antigen-binding fragment of a full antibody molecule. An antigen-binding fragment of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of an antigen-binding fragment include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed by the expression "antigen-binding fragment," as used herein.

An antigen-binding fragment of an antibody typically comprises at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_{H1}$; (ii) $V_H$-$C_{H2}$; (iii) $V_H$-$C_{H3}$; (iv) $V_H$-$C_{H1}$-$C_{H2}$; (v) $V_H$-$C_{H1}$-$C_{H2}$-$C_{H3}$; (vi) $V_H$-$C_{H2}$-$C_{H3}$; (vii) $V_H$-$C_L$; (viii) $V_L$-$C_{H1}$; (ix) $V_L$-$C_{H2}$; (x) $V_L$-$C_{H3}$; (xi) $V_L$-$C_{H1}$-$C_{H2}$; (xii) $V_L$-$C_{H1}$-$C_{H2}$-$C_{H3}$; (xiii) $V_L$-$C_{H2}$-$C_{H3}$; and (xiv) $V_L$-$C_L$. In any configuration of variable and constant domains, including any of the exemplary configurations listed here, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

The anti-SARS-CoV-2-Spike protein antibody disclosed herein may comprise one or more amino acid substitutions, insertions, and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes an antibody, and an antigen-binding fragment thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, could easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired properties such as, improved binding specificity, increased binding affinity, improved or enhanced antagonistic or agonistic biological properties (as the case may be), reduced immunogenicity, etc. Antibodies and antigen-binding fragments obtained in this general manner are encompassed by the present disclosure.

The present disclosure also includes an anti-SARS-CoV-2-Spike protein antibody comprising variants of any of the $V_H$, $V_L$, and/or CDR amino acid sequences disclosed herein having one or more conservative substitutions. For example, the present disclosure includes an anti-EPHA10 antibody having $V_H$, $V_L$, and/or CDR amino acid sequences with, e.g., 10 or fewer, 8 or fewer, 6 or fewer, 4 or fewer, etc. conservative amino acid substitutions relative to any of the $V_H$, $V_L$, and/or CDR amino acid sequences disclosed herein.

In some embodiments of the disclosure, the antibody according to the disclosure is a humanized antibody. In order to improve the binding affinity of the humanized antibody according to the disclosure, some amino acid residues in the human framework region are replaced by the corresponding amino acid residues in the species of CDRs; e.g. a rodent.

The antibodies of the present disclosure may be monospecific, bi-specific, or multispecific. Multispecific antibodies may be specific for different epitopes of one target polypeptide or may contain antigen-binding domains specific for more than one target polypeptide. The anti-SARS-CoV-2-Spike protein antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present disclosure includes bi-specific antibodies wherein one arm of an immunoglobulin is specific for SARS-CoV-2-Spike protein or a fragment thereof, and the other arm of the immunoglobulin is specific for a second therapeutic target or is conjugated to a therapeutic moiety.

In another aspect, the present disclosure provides a genetically engineered cell expressing the antibody or antigen-binding fragment thereof or containing the vector. The genetically engineered cell may be an immune cell.

In one preferred embodiments of the disclosure, the antibody or antigen-binding fragment thereof can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)).

An example of a method for manufacturing the antibody or antigen-binding fragment comprises: (a) introducing into a host cell one or more polynucleotides encoding said antibody or antigen-binding fragment; (b) culturing the host cell under conditions favorable to expression of the one or more polynucleotides; and (c) optionally, isolating the antibody or antigen-binding fragment from the host cell and/or a medium in which the host cell is grown.

A vector can be used to introduce a polynucleotides encoding the antibody or antigen-binding fragment of the invention to a host cell. In one embodiment, one type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The disclosure provides pharmaceutical compositions comprising the antibody or antigen-binding fragment thereof. The pharmaceutical compositions of the disclosure are formulated with suitable diluents, carriers, excipients, and other agents that provide improved transfer, delivery, tolerance, and the like. The compositions may be formulated for specific uses, such as for veterinary uses or pharmaceutical uses in humans. The form of the composition and the excipients, diluents and/or carriers used will depend upon the intended uses of the antibody and, for therapeutic uses, the mode of administration. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

In some embodiment of the disclosure, the pharmaceutical composition comprises a further therapeutic agent, such as an antiviral agent. The antiviral agent may be an antibody to an S protein of SARS-CoV-2; anti-inflammatory agent; an antibody to a NTD region of a S protein of SARS-CoV-2; an antibody to a HR1 region of a S protein of SARS-CoV-2; an antibody to a RBD region of a S protein of SARS-CoV-2; a SARS-CoV monoclonal antibody; a MERS-CoV monoclonal antibody; a SARS-CoV-2 monoclonal antibody; a peptide; a protease inhibitor; a PIKfyve inhibitor; a TMPRSS2 inhibitor; and a cathepsin inhibitor; a furin inhibitor; an antiviral peptide; an antiviral protein; an antiviral chemical compound. For example, the antiviral agent may be at least one selected from the group consisting of: 1A9; 201; 311mab-31B5; 311mab-32D4; 47D11; 4A8; 4C2; 80R; Apilimod; B38; camostat mesylate; Casirivimab; CR3014; CR3022; D12; E-64D; EK1; EK1C4; H4; HR2P; IBP02; Imdevimab; m336; MERS-27; MERS-4; MI-701; n3088; n3130; P2B-2F6; P2C-1F11; PI8; S230; S309; SARS-CoV-2 S HR2P fragment (aa1 168-1203); Tetrandrine; Viracept (nelfinavir mesylate); YM201636; a-1-PDX; favipiravir; IFN-a; IFN-alb; IFN-a2a; lopinavir-ritonavir; Q-Griffithsin (Q-GRFT); and Griffithsin; oseltamivir; zanamivir; abacavir; zidovudine; zalcitabine; didanosine; stavudine; efavirenz; indinavir; ritonavir; nelfinavir; amprenavir; ribavirin; Remdesivir; chloroquine; hydroxychloroquine; rIFN-alpha-2a; rIFN-beta-lb; rIFN-gamma; nIFN-alpha; nIFN-beta; nIFN-gamma; IL-2; PD-L1; Anti-PD-Ll; a checkpoint inhibitor; an interferon; interferon mixture; recombinant or natural interferon; Alferon; alpha-interferon species; recombinant or natural interferon alpha; recombinant or natural interferon alpha 2a; recombinant or natural interferon beta; recombinant or natural interferon beta lb; and recombinant or natural interferon gamma. The alpha-interferon species may be a mixture of at least seven species of alpha-interferon produced by human white blood cells, wherein the seven species are: interferon alpha 2; interferon alpha 4; interferon alpha 7; interferon alpha 8; interferon alpha 10; interferon alpha 16; and interferon alpha 17.

The dose of antibody administered to a patient may vary depending upon the age and the size of the patient, target disease, conditions, route of administration, and the like. The preferred dose is typically calculated according to body weight or body surface area. When an antibody of the present disclosure is used for treating a condition or disease associated with EPHA10 in an adult patient, it may be advantageous to intravenously administer the antibody of the present disclosure. Depending on the severity of the condition, the frequency and the duration of the treatment can be adjusted. Effective dosages and schedules for administering the antibody may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present disclosure can be delivered subcutaneously or intravenously with a vessel or injection device such as standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138).

Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described here in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

The present disclosure provides a method for detecting a coronavirus in a sample comprising contacting the sample with the antibody or antigen-binding fragment thereof.

The present disclosure provides a method for neutralizing a coronavirus in a subject in need, comprises administering to the subject the antibody or antigen-binding fragment thereof.

The present disclosure provides a kit for detecting a coronavirus in a sample, wherein the kit comprises the antibody or antigen-binding fragment thereof.

The anti-SARS-CoV-2-Spike protein antibody of the present disclosure may also be used to detect and/or measure coronavirus, or SARS-CoV-2-Spike protein-expressing cells in a sample, e.g., for diagnostic purposes. For example, an anti-SARS-CoV-2-Spike protein antibody, or fragment thereof, may be used to diagnose a condition or disease characterized by coronavirus infection. Exemplary diagnostic assays for coronavirus may comprise, e.g., contacting a sample, obtained from a patient, with an anti-SARS-CoV-2-Spike protein antibody of the disclosure, wherein the anti-SARS-CoV-2-Spike protein antibody is labeled with a detectable label or reporter molecule. Alternatively, an unlabeled anti-SARS-CoV-2-Spike protein antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure coronavirus in a sample include enzyme-linked immunosorbent assay (ELISA), radioimmunoassay (RIA), and fluorescence-activated cell sorting (FACS).

The following examples are provided to aid those skilled in the art in practicing the present disclosure.

EXAMPLES

Material and Method

FACS analysis and sorting of spike-specific B cells. Splenocytes isolated from Sing immunized mice were incubated with 2 μg/ml S protein at 4° C. for 1 h, followed by washing and incubation with an antibody cocktail against CD19 (clone: 6D5, PE-Cy7-conjugated, Biolegend), CD3 (clone: 17A2, PE-conjugated, Biolegend), and His (clone: J095G46, APC-conjugated, Biolegend,), at 4° C. for 15 min. Propidium Iodide (Biolegend) was used to exclude dead cells. Live single spike-specific B cells (CD3 CD19) were sorted into 96-well PCR plates (Applied Biosystems) containing 10 μl/well catch buffer (10 mM Tris-HCl, pH 8, amd 5 U/μl RNasin (Promega)) by BD FACSAria II. For repertoire analysis, five spleens from $S_{mg}$ or $S_{fg}$ immunized mice were pooled and stained before sorting.

Single-B cell screening. Primers were designed based on a previous publication. The reaction was then performed at 50° C. for 30 min, 95° C. for 15 min followed by 40 cycles at 94° C. for 30 s, 50° C. for 30 s, 72° C. for 1 min, and final incubation at 72° C. for 10 min. Semi-nested second round PCR was performed using KOD One PCR master mix (TOYOBO) with 1 μl of unpurified first round PCR product at 98° C. for 2 min followed by 45 cycles of 98° C. for 10 s, 55° C. for 10 s, 68° C. for 10 s, and final incubation at 68° C. for 1 min. PCR products were then analyzed on 1.5% agarose gels and sequencing. The Ig V and L genes were identified by searching on IMGT website (http://imgt.org/IMGT_vquest/input). The genes were then amplified from second round PCR product with single gene-specific V and L gene primers containing restriction sites for cloning into the vectors containing human IgH or IgL expression backbone. The chimeric IgH and IgL expression constructions were co-transfected into Expi293 for antibody production.

Binding of antibody with S protein expressing 293T surface. 293T cells were transfected with pcDNA6/Spike-P2A-eGFP. Transfected cells were selected under 10 μg/ml of blasticidin for 2-3 weeks. Selected cells were then sorted by FACSAria II to obtain eGFP expressing cells. These cells were maintained in DMEM containing 10% FBS and 10 μg/ml of blasticidin. 2-3×10$^5$ cells were incubated with serially diluted antibody in FACS buffer on ice for 1 h. Then, cells were washed with FACS buffer for 3 times, followed by staining in BV421 mouse anti-human IgG (BD Biosciences, 562581, 1:100) on ice for 20 min and washed with FACS buffer twice. The percentage of positive cells was quantified using FACS Canto II and the data were analyzed with FlowJo. The S protein variants used here are: WH01 spike: original S protein; D614G: D614G; B.1.1.7: 69-70 deletion, 144 deletion, N501Y, A570D, D614G, P681H, T716I, S982A and D1118H; B.1.351: L18F, D80A, D215G, 242-244 deletion, R246I, K417N, E484K, N501Y, D614G and A701V; BA.1.

Affinity and avidity determination using Octet (bio-layer interferometry). Fab fragment was prepared by using Pierce Fab Micro Preparation Kit (ThermoFisher Scientific) according to manufacturer's instructions. Briefly, m31A7 IgG (250 μg) was digested by incubating with immobilized papain resin at 37° C. for 8 h. Fab was then purified by protein A column. Purified m31A7 IgG or Fab fragments was loaded at 10 or 6.7 μg/ml kinetics buffer (0.01% endotoxin-free BSA, 0.002% Tween-20, 0.005% NaN$_3$ in PBS) onto Protein G or FAB2G biosensors (Molecular Devices, ForteBio), respectively. Association and dissociation of S protein (SARS-CoV-2 WH01) by both IgG or Fab was performed in kinetics buffer at indicated concentrations for 5 min and 15 min, respectively. $K_D$ values were calculated using a 1:1 global fit model (Octet).

Results

Figure 1B:
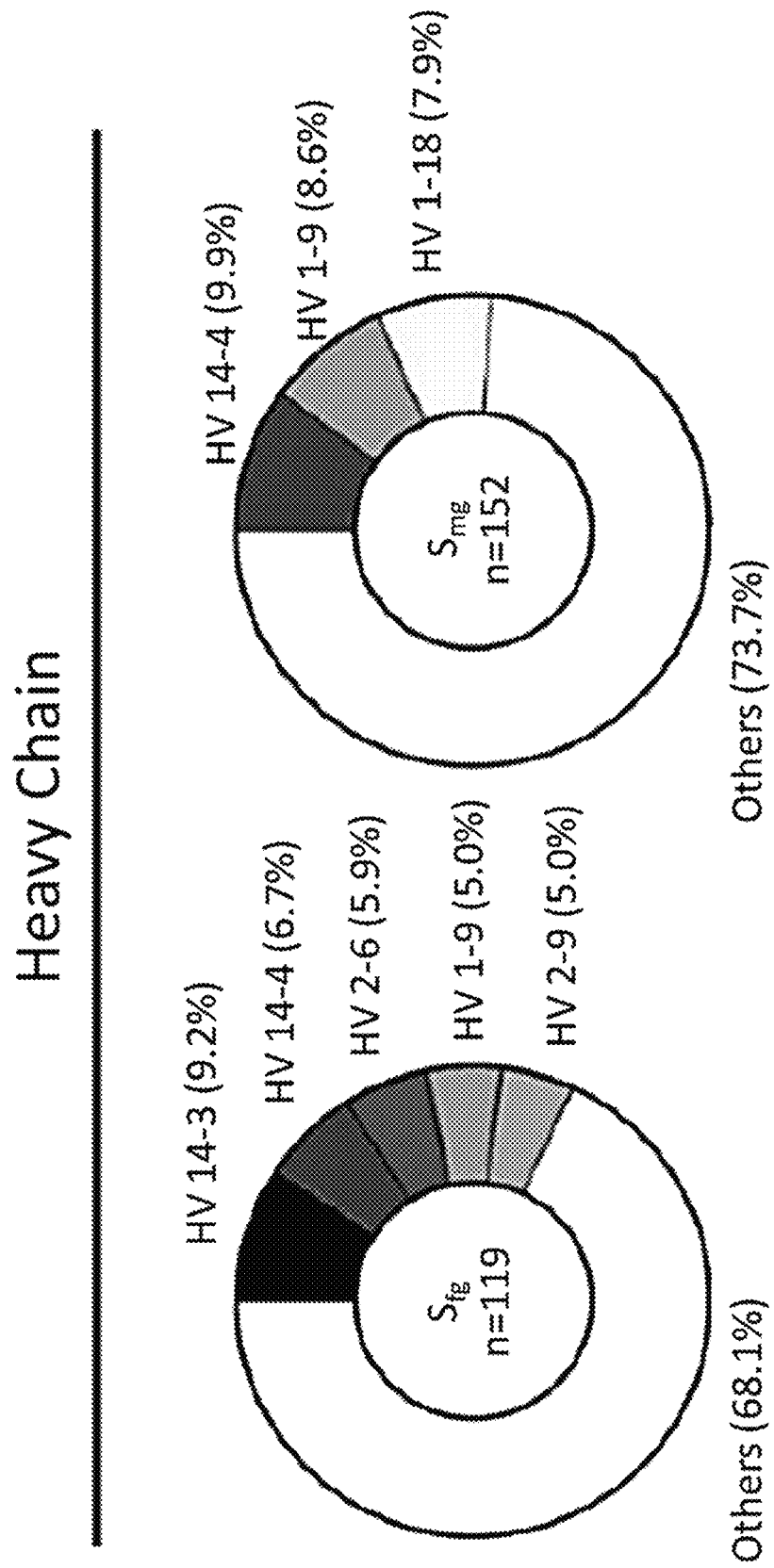
Figure 1C:
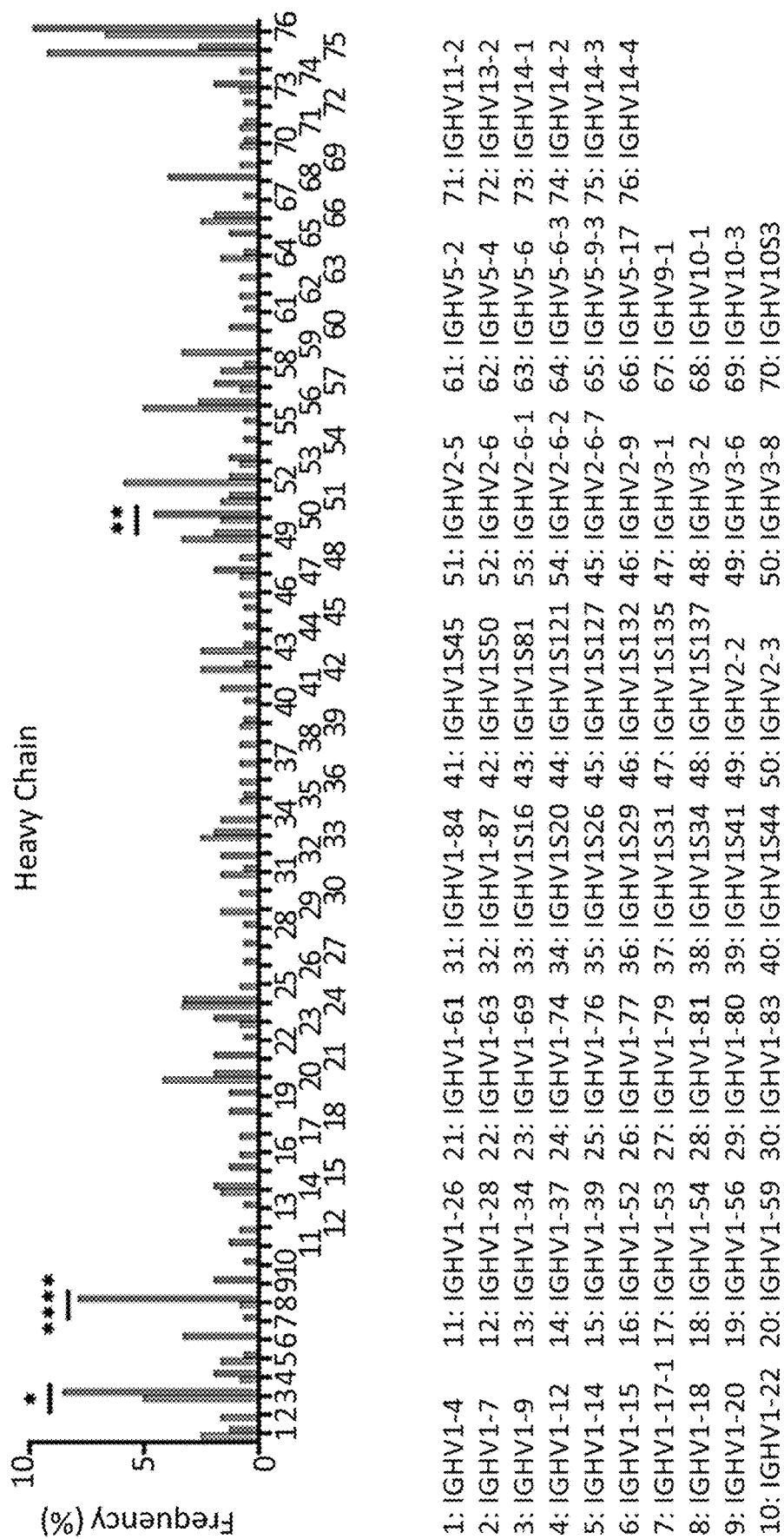
Figure 2A:
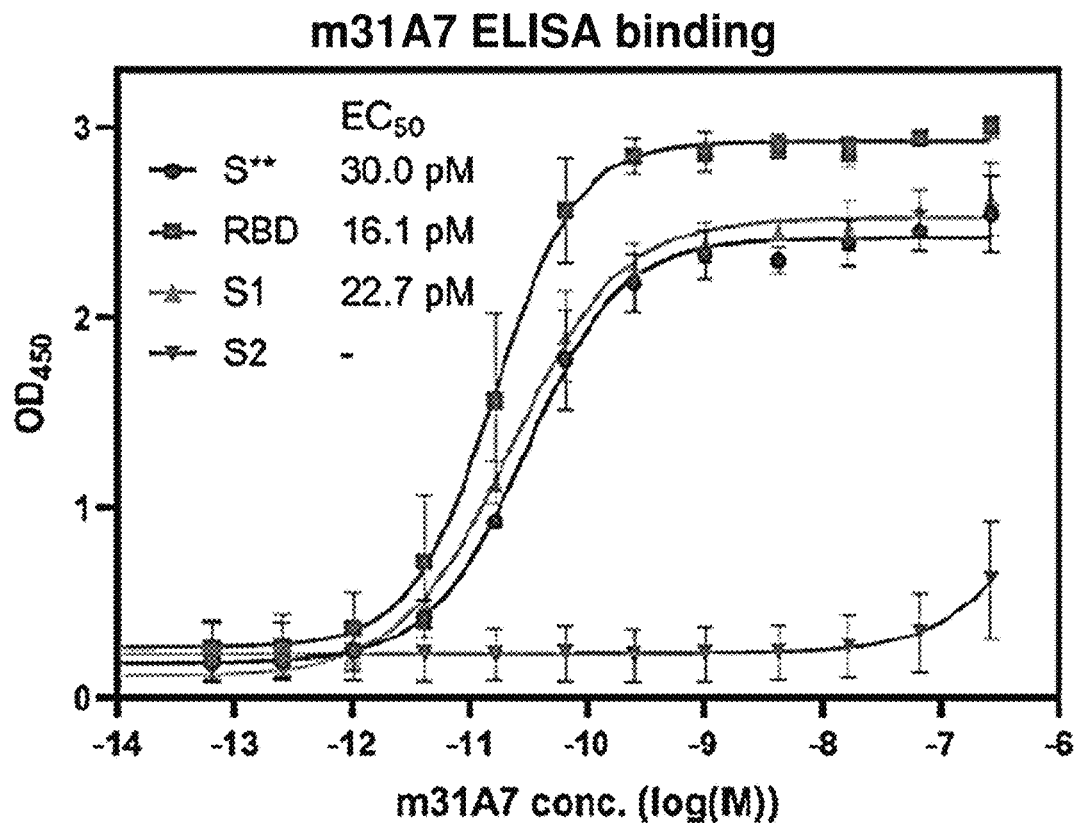
FIGS. 2A to 2B show the binding of m31A7 with SARS-CoV-2 Spike protein.
Figure 2B:
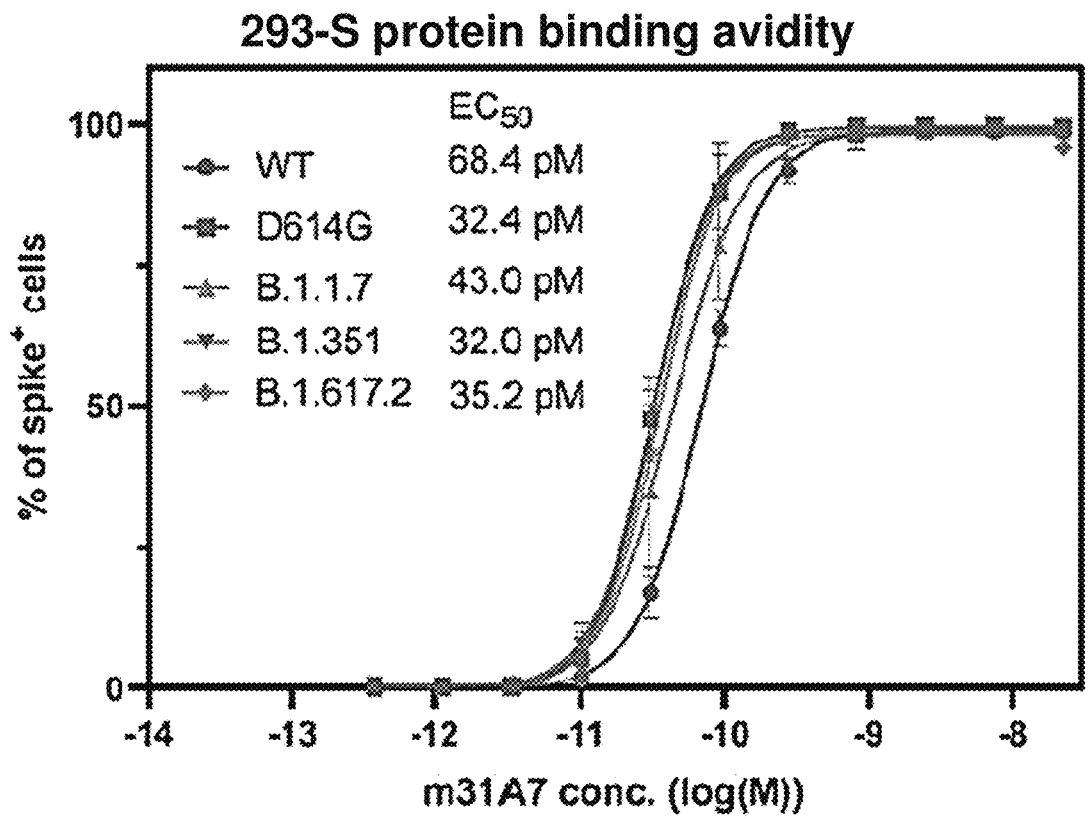
Figure 3A:
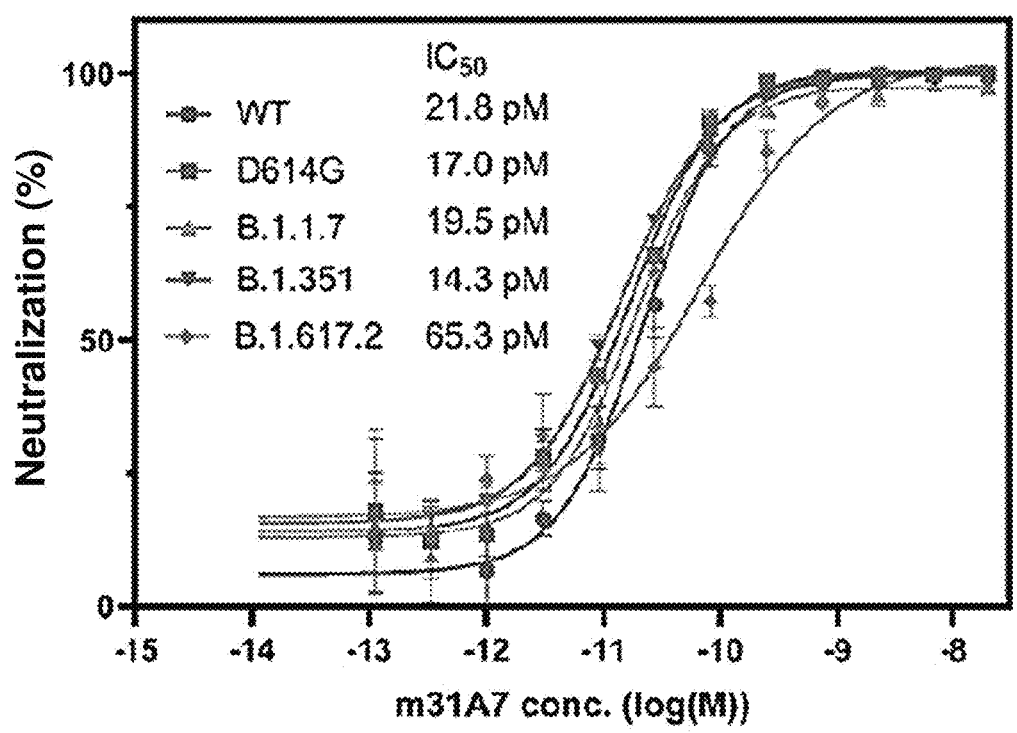
FIGS. 3A and 3B show that m31A7 is able to neutralize various variants of SARS-CoV-2 pseudoviruses.
Figure 3B:
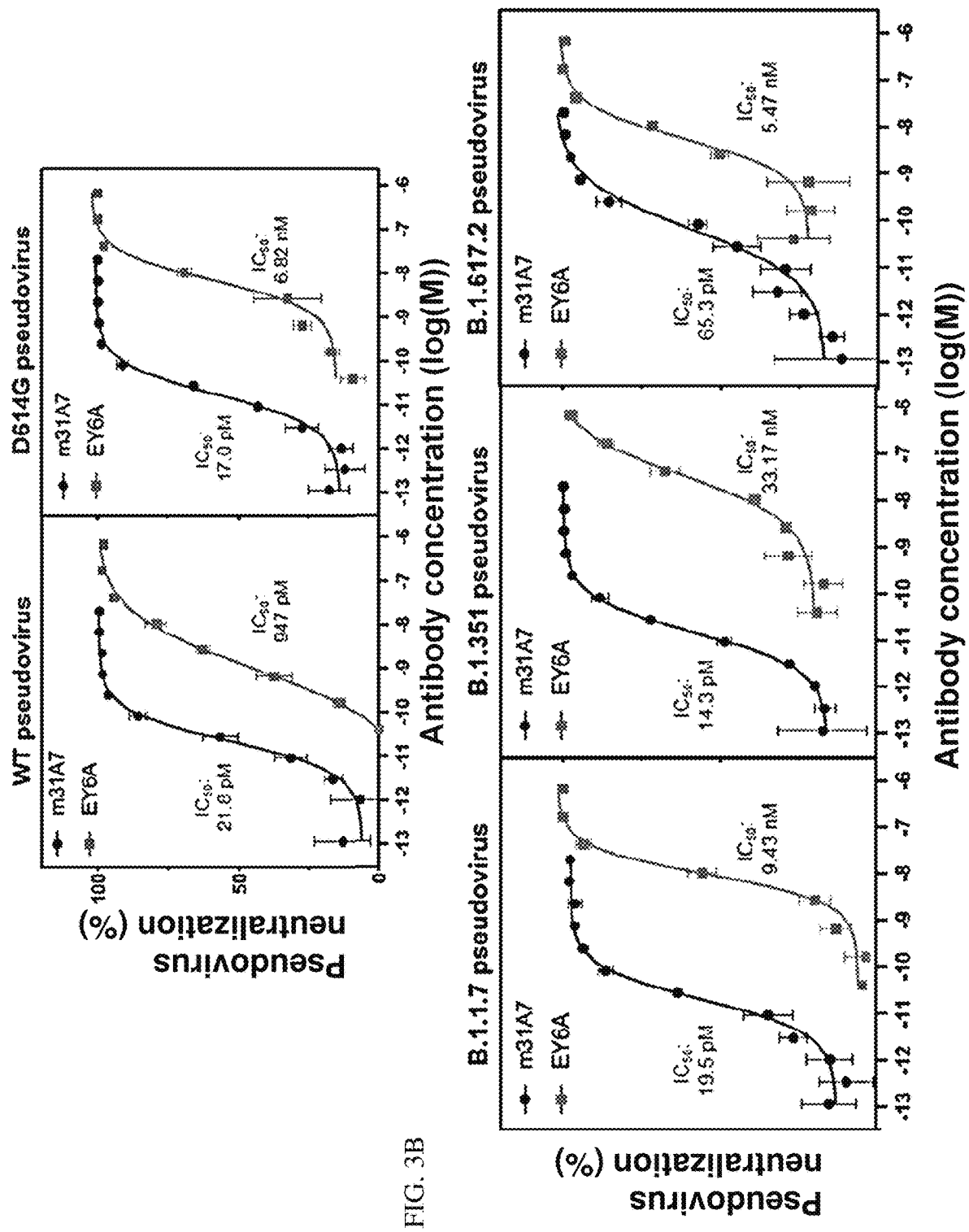
Figure 4A:
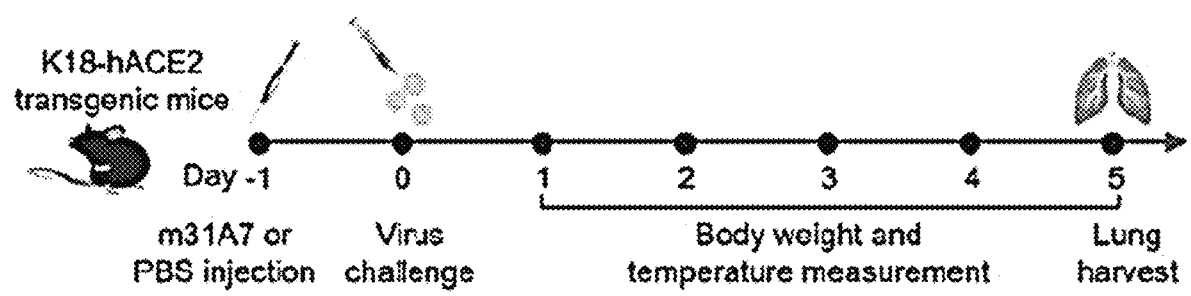
FIGS. 4A to 4C exhibit that m31A7 shows prophylactic activity against SARS-CoV-2 challenge in vivo.
Figure 4B:
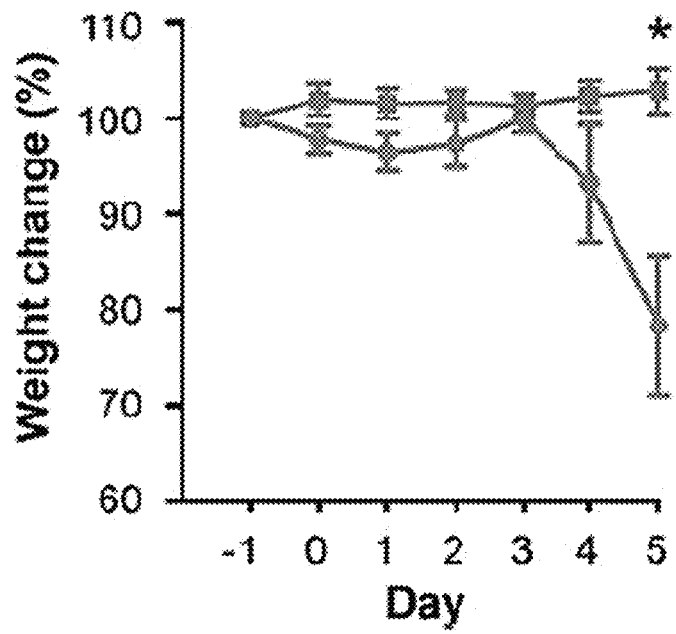
Figure 4C:
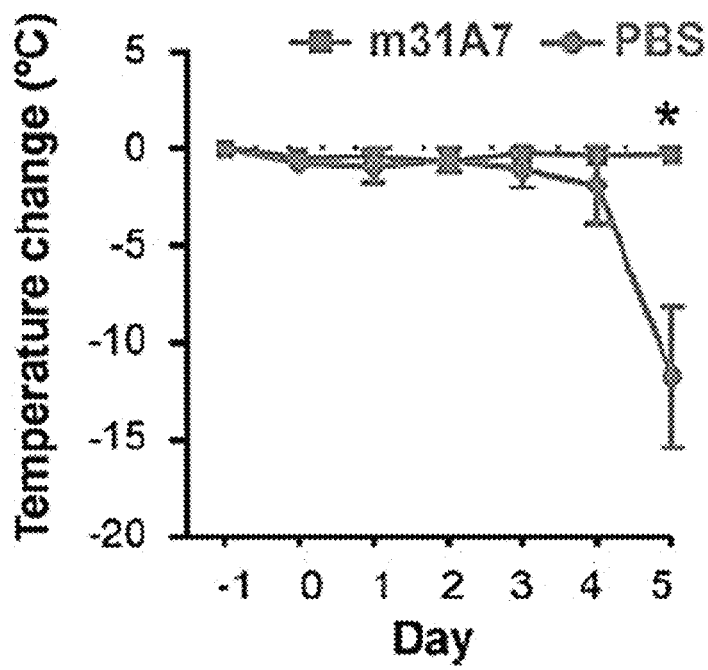
Figure 5A:
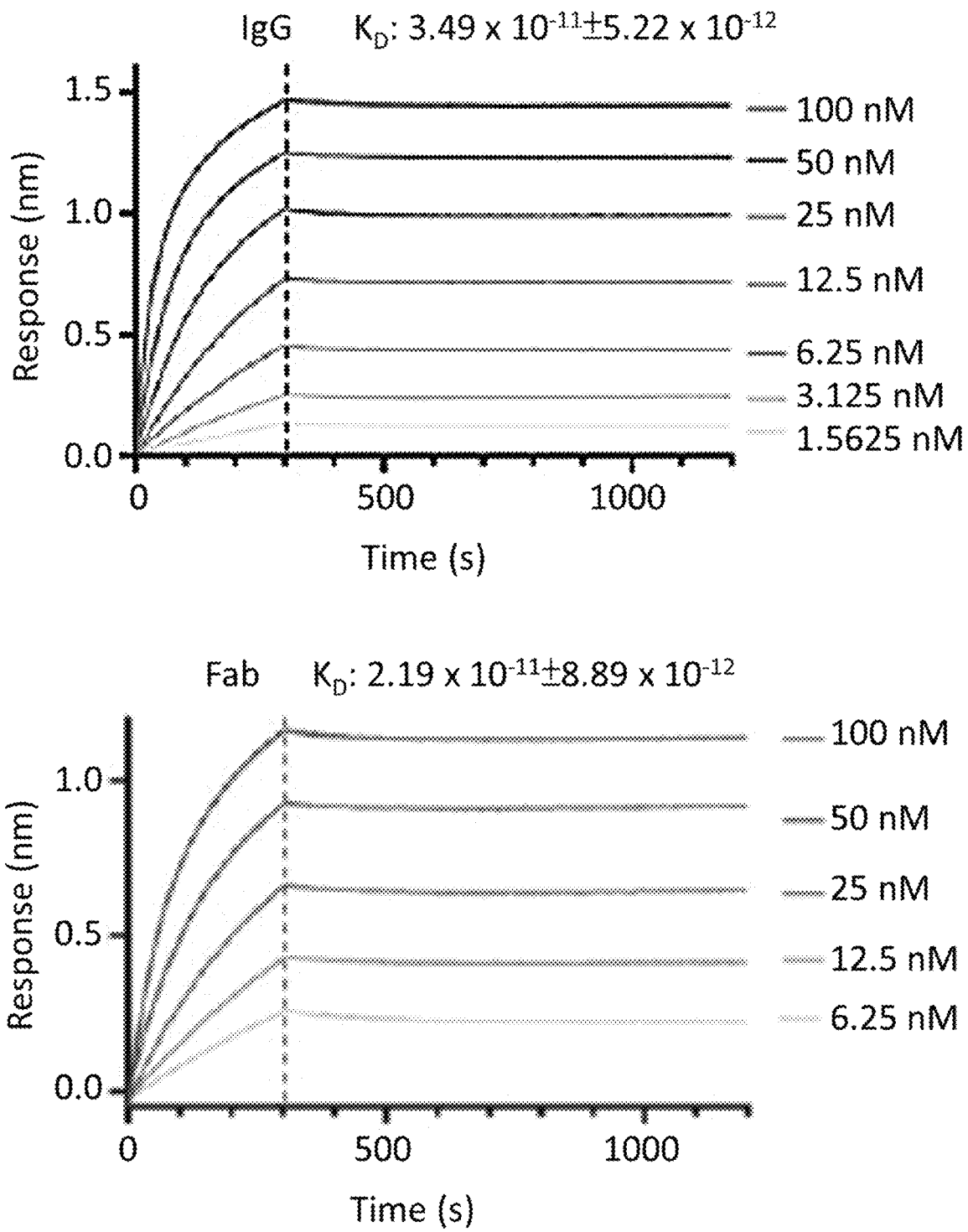
FIGS. 5A to 5D show biophysical properties of m31A7.
Figure 5B:
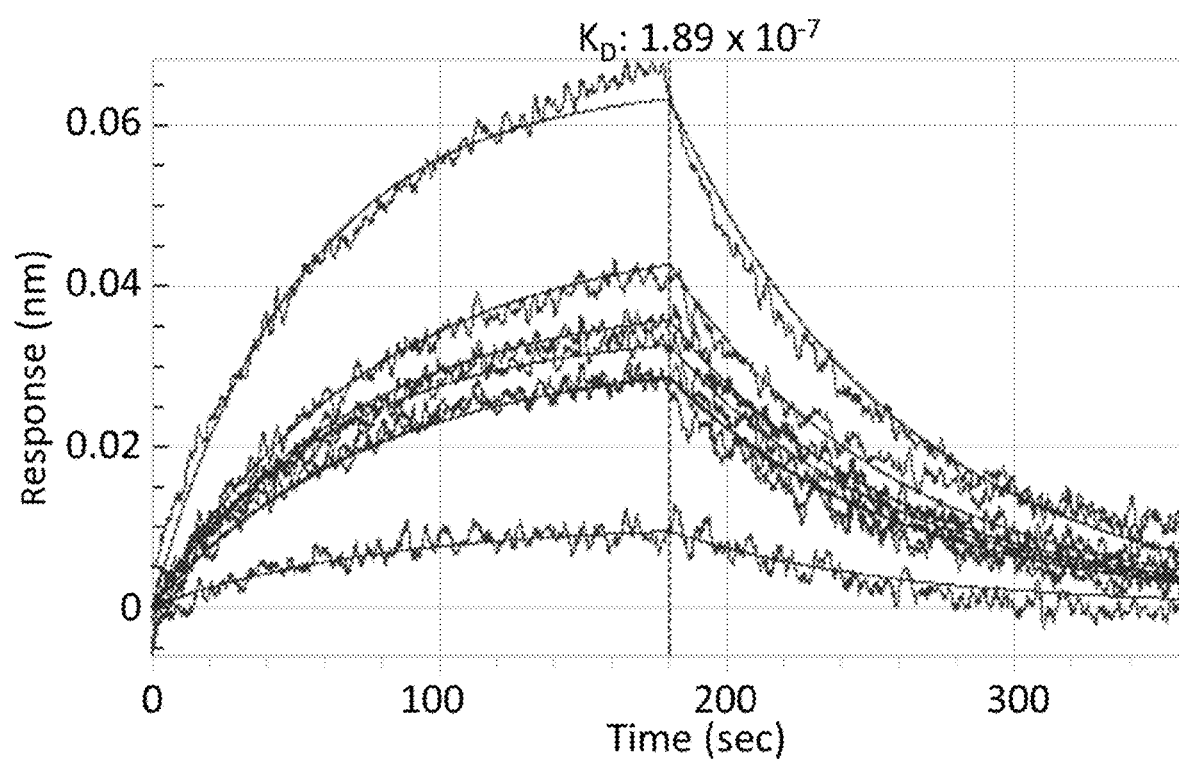
Figure 5C:
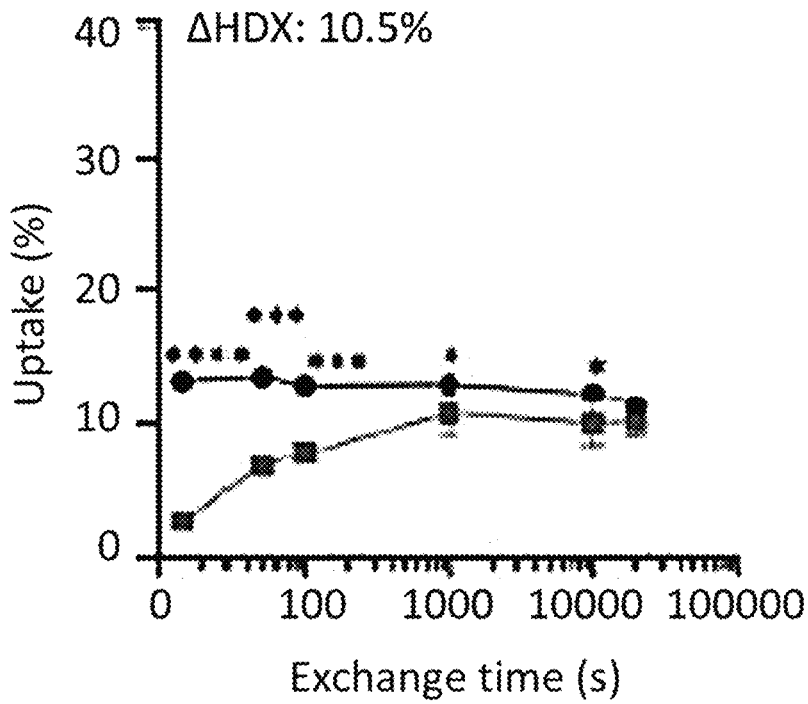
Figure 5C:
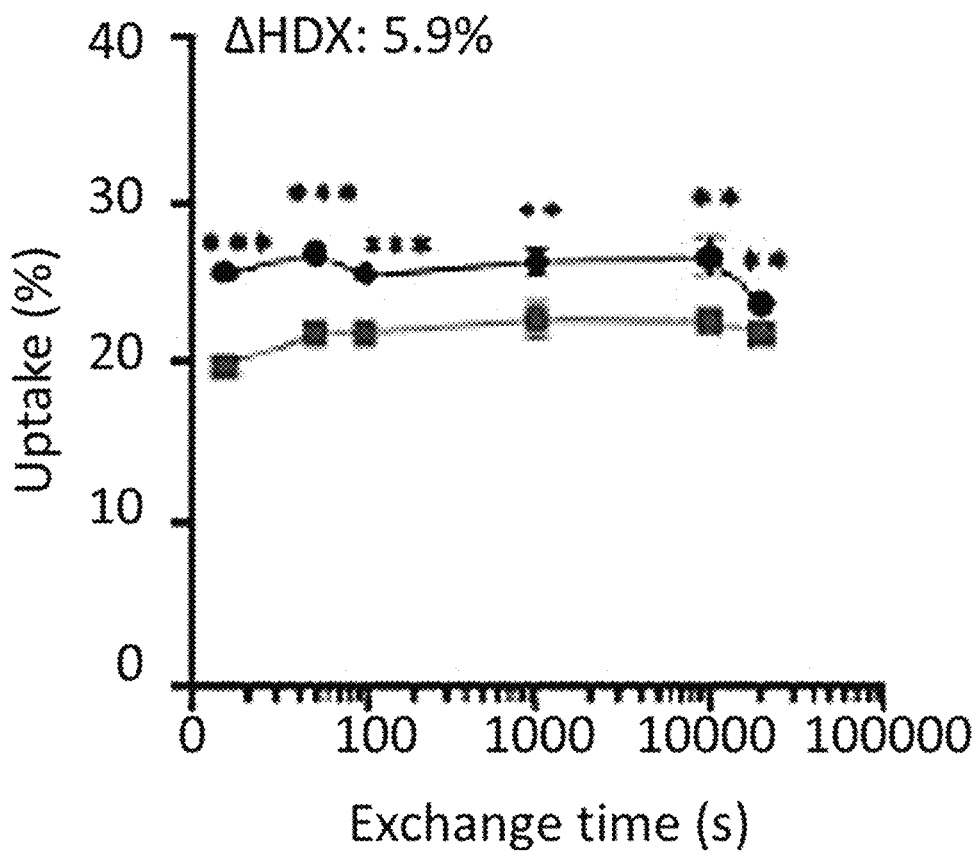
Figure 5C:
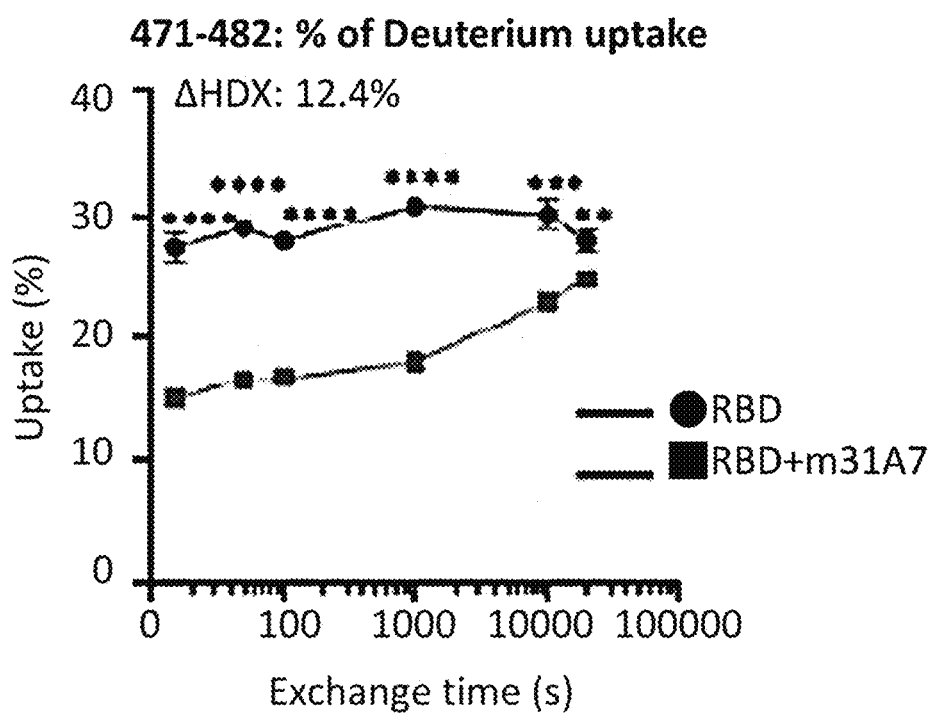
Figure 5D:
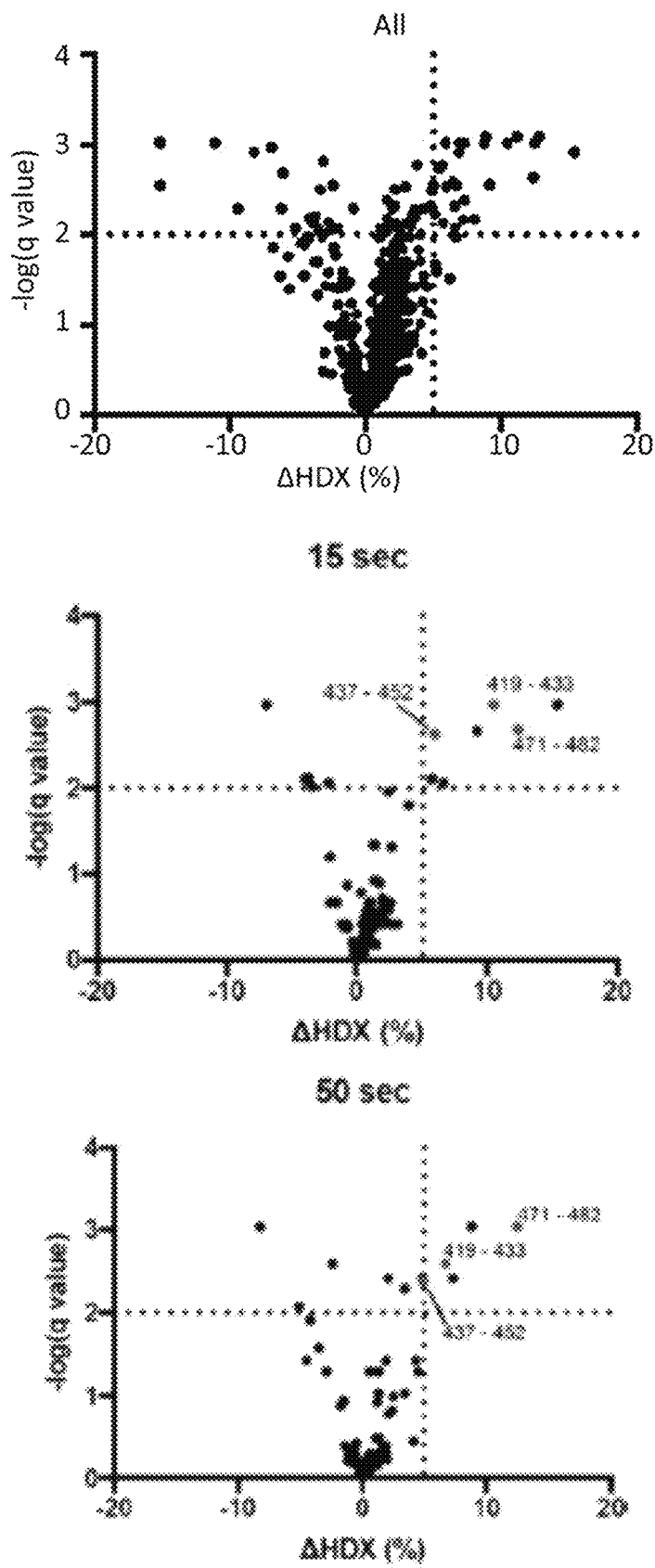

We here aim to isolate spike specific monoclonal antibodies from mice immunized with the monoglycosylated state ($S_{mg}$) of SARS-CoV-2. We also compared the spike-specific B cell repertoire between $S_{mg}$ and fully glycosylated Spike ($S_{fg}$) immunized mice. The sorting of S protein-specific B cells from $S_{mg}$ immunized mice led to the identification of a monoclonal antibody (mAb) m31A7 from IGHV1-18 amplified clones (FIG. 1A). Heavy chain repertoire analysis of spike-specific B cells isolated from $S_{mg}$ and $S_{fg}$ immunized mice revealed that several heavy chain loci, including IGHV1-9, IGHV1-18 and IGHV2-3, were selectively expanded in $S_{mg}$ immunized mice (FIGS. 1B and 1C). This m31A7 mAb interacts with the full-length S protein, S1 and RBD, but not S2 (FIG. 2A) and binds to HEK293T cells that express the S protein from different SARS-CoV-2 variants (FIG. 2B). In addition, m31A7 was shown to neutralize various pseudovirus variants (WT, D614G, Alpha, Beta, and Delta) at sub-picomolar $IC_{50}$ which is up to 1000-fold higher than the reported human mAb EY6A (D. Zhou et al., Structural basis for the neutralization of SARS-CoV-2 by an antibody from a convalescent patient. Nat Struct Mol Biol 27, 950-958 (2020)) (FIGS. 3A and 3B). A prophylactic study also demonstrated good in vivo efficacy of m31A7 in K18hACE2 transgenic mice (FIG. 4A) in maintaining both body weight and temperature after challenge with SARS-CoV-2 virus (FIGS. 4B and 4C). Bio-layer interferometry (BLI) analysis measured the dissociation constant of m31A7 and its Fab binding to S protein at 34.9 pM and 0.22 nM, respectively (FIG. 5A). Binding avidity of full-length m31A7 IgG1 to full-length Omicron BA.1 S protein was measured by bio-layer interferometry and shown in FIG. 5B. Epitope mapping by hydrogen-deuterium exchange mass spectrometry (HDX-MS) showed the binding regions on RBD (FIGS. 5C and 5D). The extremely low usage of IGHV1-18 in the $S_{fg}$ B cell repertoire (FIGS. 1A and 1B) suggested that $S_{fg}$ may not elicit m31A7 or related antibodies.

While the present disclosure has been described in conjunction with the specific embodiments set forth, many alternatives thereto and modifications and variations thereof will be apparent to those of ordinary skill in the art. All such alternatives, modifications and variations are regarded as falling within the scope of the present disclosure.

What is claimed is:

1. A complex comprising an antibody or antigen-binding fragment thereof that is specific for an epitope in a spike protein of a CoV; wherein the epitope comprises a part locating in 419 to 433 amino acid residues or 471 to 482 amino acid residues of SEQ ID NO: 8, wherein the antibody or antigen-binding fragment thereof comprises complementarity determining regions (CDRs) of a heavy chain variable region and complementarity determining regions of a light chain variable region, wherein the complementarity determining regions of the heavy chain variable region comprise CDRH1, CDRH2, and CDRH3 regions, and the complementarity determining regions of the light chain variable region comprise CDRL1, CDRL2, and CDRL3 regions, wherein the CDRH1 region comprises the amino acid sequence of SEQ ID NO: 1; the CDRH2 region comprises the amino acid sequence of SEQ ID NO: 2; the CDRH3 region comprises the amino acid sequence of SEQ ID NO: 3; and wherein the CDRL1 region comprises the amino acid sequence of SEQ ID NO: 4; the CDRL2 region comprises the amino acid sequence of WAS; the CDRL3 region comprises the amino acid sequence of SEQ ID NO: 5.

2. The complex of claim 1, wherein the spike protein is fully glycosylated.

3. The complex of claim 1, wherein the antibody or antigen-binding fragment thereof comprises a heavy chain variable region comprising the amino acid sequence of SEQ ID NO: 6; and a light chain variable region comprising the amino acid sequence of SEQ ID NO: 7.

4. The complex of claim 1, wherein the antibody is a monoclonal antibody, chimeric antibody, humanized antibody or human antibody.

5. The complex of claim 1, wherein the antibody is multispecific.

6. The complex of claim 1, wherein the CoV is alpha-CoV, beta-CoV, gamma-CoV, and delta-CoV2.

7. The complex of claim 1, wherein the CoV is SARS-CoV, MERS-CoV or SARS-CoV-2.

8. A method for treating infection with a coronavirus in a subject in need thereof, comprising administering a therapeutically effective amount of the antibody or antigen-binding fragment thereof of claim 1.

9. The method of claim 8, wherein the method comprises injecting the antibody or antigen-binding fragment thereof into the body of the subject subcutaneously, intravenously, or intramuscularly.

10. The method of claim 8, wherein the method neutralizes a coronavirus in the subject in need thereof.

11. A vector encoding the antibody or antigen-binding fragment thereof of claim 1.

12. The vector of claim 11, wherein the vector is a plasmid or a viral vector.

* * * * *

SEQUENCE LISTING

```
Sequence total quantity: 8
SEQ ID NO: 1            moltype = AA  length = 8
FEATURE                 Location/Qualifiers
source                  1..8
                        mol_type = protein
                        organism = Mus musculus
SEQUENCE: 1
GYTFTEYT                                                                    8

SEQ ID NO: 2            moltype = AA  length = 8
FEATURE                 Location/Qualifiers
source                  1..8
                        mol_type = protein
                        organism = Mus musculus
SEQUENCE: 2
INPNIGDT                                                                    8

SEQ ID NO: 3            moltype = AA  length = 11
FEATURE                 Location/Qualifiers
source                  1..11
                        mol_type = protein
                        organism = Mus musculus
SEQUENCE: 3
AREVYNYSFA Y                                                               11

SEQ ID NO: 4            moltype = AA  length = 12
FEATURE                 Location/Qualifiers
source                  1..12
                        mol_type = protein
                        organism = Mus musculus
SEQUENCE: 4
QSLLYSSNQK NY                                                              12

SEQ ID NO: 5            moltype = AA  length = 9
FEATURE                 Location/Qualifiers
source                  1..9
                        mol_type = protein
                        organism = Mus musculus
SEQUENCE: 5
QQYYRYPLT                                                                   9

SEQ ID NO: 6            moltype = AA  length = 465
FEATURE                 Location/Qualifiers
source                  1..465
                        mol_type = protein
                        organism = Mus musculus
```

```
SEQUENCE: 6
MGWSLILLFL  VAVATRVEVQ  LQQSGPEMVK  PGASVKISCK  TSGYTFTEYT  IYWVKQSHGK   60
SLEWLGGINP  NIGDTTYNQK  FKGKATLTVD  TSSSTAYMEL  RSLTSEDSAV  YYCAREVYNY  120
SFAYWGQGTL  VTVSAASTKG  PSVFPLAPSS  KSTSGGTAAL  GCLVKDYFPE  PVTVSWNSGA  180
LTSGVHTFPA  VLQSSGLYSL  SSVVTVPSSS  LGTQTYICNV  NHKPSNTKVD  KKAEPKSCDK  240
THTCPPCPAP  ELLGGPSVFL  FPPKPKDTLM  ISRTPEVTCV  VVDVSHEDPE  VKFNWYVDGV  300
EVHNAKTKPR  EEQYNSTYRV  VSVLTVLHQD  WLNGKDYKCK  VSNKALPAPI  EKTISKAKGQ  360
PREPQVYTLP  PSRDELTRNQ  VSLTCLVKGF  YPSDIAVEWE  SNGQPENNYK  TTPPVLDSDG  420
SFFLYSKLTV  DKSRWQQGNV  FSCSVMHEAL  HNHYTQKSLS  LSPGK                   465

SEQ ID NO: 7            moltype = AA   length = 240
FEATURE                 Location/Qualifiers
source                  1..240
                        mol_type = protein
                        organism = Mus musculus
SEQUENCE: 7
MRVPAQLLGL  LLLWLPGARC  DIVMSQSPSS  LAVSVGEKVT  MSCKSSQSLL  YSSNQKNYLA   60
WYQQKLGQTP  KLLIYWASSR  ESGVPDRFTG  SGSGTDFTLT  ISSVRAEDLA  VYYCQQYYRY  120
PLTFGVGTKL  ELKRTVAAPS  VFIFPPSDEQ  LKSGTASVVC  LLNNFYPREA  KVQWKVDNAL  180
QSGNSQESVT  EQDSKDSTYS  LSSTLTLSKA  DYEKHKVYAC  EVTHQGLSSP  VTKSFNRGEC  240

SEQ ID NO: 8            moltype = AA   length = 1236
FEATURE                 Location/Qualifiers
source                  1..1236
                        mol_type = protein
                        organism = SARS-CoV-2
SEQUENCE: 8
QCVNLTTRTQ  LPPAYTNSFT  RGVYYPDKVF  RSSVLHSTQD  LFLPFFSNVT  WFHAIHVSGT   60
NGTKRFDNPV  LPFNDGVYFA  STEKSNIIRG  WIFGTTLDSK  TQSLLIVNNA  TNVVIKVCEF  120
QFCNDPFLGV  YYHKNNKSWM  ESEFRVYSSA  NNCTFEYVSQ  PFLMDLEGKQ  GNFKNLREFV  180
FKNIDGYFKI  YSKHTPINLV  RDLPQGFSAL  EPLVDLPIGI  NITRFQTLLA  LHRSYLTPGD  240
SSSGWTAGAA  AYYVGYLQPR  TFLLKYNENG  TITDAVDCAL  DPLSETKCTL  KSFTVEKGIY  300
QTSNFRVQPT  ESIVRFPNIT  NLCPFGEVFN  ATRFASVYAW  NRKRISNCVA  DYSVLYNSAS  360
FSTFKCYGVS  PTKLNDLCFT  NVYADSFVIR  GDEVRQIAPG  QTGKIADYNY  KLPDDFTGCV  420
IAWNSNNLDS  KVGGNYNYLY  RLFRKSNLKP  FERDISTEIY  QAGSTPCNGV  EGFNCYFPLQ  480
SYGFQPTNGV  GYQPYRVVVL  SFELLHAPAT  VCGPKKSTNL  VKNKCVNFNF  NGLTGTGVLT  540
ESNKKFLPFQ  QFGRDIADTT  DAVRDPQTLE  ILDITPCSFG  GVSVITPGTN  TSNQVAVLYQ  600
DVNCTEVPVA  IHADQLTPTW  RVYSTGSNVF  QTRAGCLIGA  EHVNNSYECD  IPIGAGICAS  660
YQTQTNSPGS  AGSVASQSII  AYTMSLGAEN  SVAYSNNSIA  IPTNFTISVT  TEILPVSMTK  720
TSVDCTMYIC  GDSTECSNLL  LQYGSFCTQL  NRALTGIAVE  QDKNTQEVFA  QVKQIYKTPP  780
IKDFGGFNFS  QILPDPSKPS  KRSFIEDLLF  NKVTLADAGF  IKQYGDCLGD  IAARDLICAQ  840
KFNGLTVLPP  LLTDEMIAQY  TSALLAGTIT  SGWTFGAGAA  LQIPFAMQMA  YRFNGIGVTQ  900
NVLYENQKLI  ANQFNSAIGK  IQDSLSSTAS  ALGKLQDVVN  QNAQALNTLV  KQLSSNFGAI  960
SSVLNDILSR  LDPPEAEVQI  DRLITGRLQS  LQTYVTQQLI  RAAEIRASAN  LAATKMSECV 1020
LGQSKRVDFC  GKGYHLMSFP  QSAPHGVVFL  HVTYVPAQEK  NFTTAPAICH  DGKAHFPREG 1080
VFVSNGTHWF  VTQRNFYEPQ  IITTDNTFVS  GNCDVVIGIV  NNTVYDPLQP  ELDSFKEELD 1140
KYFKNHTSPD  VDLGDISGIN  ASVVNIQKEI  DRLNEVAKNL  NESLIDLQEL  GKYEQDIRSL 1200
VPRGSPGSGY  IPEAPRDGQA  YVRKDGEWVL  LSTFLG                             1236
```